United States Patent
Kang et al.

(10) Patent No.: US 9,700,268 B2
(45) Date of Patent: Jul. 11, 2017

(54) X-RAY IMAGING APPARATUS AND CONTROL METHOD FOR THE SAME

(71) Applicant: SAMSUNG ELECTRONICS CO., LTD., Suwon-si (KR)

(72) Inventors: Dong Goo Kang, Hwaseong-si (KR); Hyun Hwa Oh, Hwaseong-si (KR); Sung Hoon Kang, Suwon-si (KR); Young Hun Sung, Hwaseong-si (KR); Kang Ho Lee, Hwaseong-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 247 days.

(21) Appl. No.: 14/513,370

(22) Filed: Oct. 14, 2014

(65) Prior Publication Data
US 2015/0103976 A1   Apr. 16, 2015

(30) Foreign Application Priority Data
Oct. 14, 2013   (KR) .................. 10-2013-0121832

(51) Int. Cl.
*A61B 6/00* (2006.01)
*A61B 6/04* (2006.01)

(52) U.S. Cl.
CPC ............ *A61B 6/4241* (2013.01); *A61B 6/482* (2013.01); *A61B 6/5205* (2013.01); *A61B 6/542* (2013.01); *A61B 6/0414* (2013.01)

(58) Field of Classification Search
CPC ..... A61B 6/4241; A61B 6/482; A61B 6/5205; A61B 6/542
See application file for complete search history.

(56) References Cited

U.S. PATENT DOCUMENTS

| | | | |
|---|---|---|---|
| 2009/0129537 A1 | 5/2009 | Rao et al. | |
| 2009/0220043 A1 | 9/2009 | Nishide et al. | |
| 2009/0290680 A1* | 11/2009 | Tumer | G01T 1/247 378/62 |
| 2010/0020922 A1 | 1/2010 | Carmi | |
| 2014/0185762 A1* | 7/2014 | Lee | G01N 23/04 378/62 |
| 2014/0321603 A1* | 10/2014 | Taguchi | A61B 6/032 378/5 |
| 2014/0353513 A1* | 12/2014 | Partain | G01T 1/2018 250/366 |

FOREIGN PATENT DOCUMENTS

| | | |
|---|---|---|
| JP | 2009-300295 A | 12/2009 |
| JP | 2011-130929 A | 7/2011 |

* cited by examiner

*Primary Examiner* — Dani Fox
(74) *Attorney, Agent, or Firm* — Sughrue Mion, PLLC

(57) ABSTRACT

An X-ray imaging apparatus and control method for the X-ray imaging apparatus are provided. The X-ray imaging apparatus includes an X-ray source configured to generate and emit X-rays having a preset broadband, an X-ray detector including a plurality of raw pixels configured to detect an average of ten photons or less in response to the X-rays which are emitted and convert the detected photons into an electrical signal, and an image processor configured to produce a plurality of single-energy images corresponding respectively to a plurality of preset energy bands by separating the plurality of raw pixels for each of the plurality of preset energy bands based on the electrical signal, and to produce a multi-energy image using the single-energy images.

22 Claims, 19 Drawing Sheets

X-RAY IMAGING APPARATUS AND CONTROL METHOD FOR THE SAME

CROSS-REFERENCE TO RELATED APPLICATION

This application claims priority from Korean Patent Application No. 2013-0121832, filed on Oct. 14, 2013 in the Korean Intellectual Property Office, the disclosure of which is incorporated herein by reference it its entirety.

BACKGROUND

1. Field

Apparatuses and methods consistent with the exemplary embodiments relate to an X-ray imaging apparatus to produce an X-ray image by transmitting X-rays through an object, and a control method for the same.

2. Description of the Related Art

An X-ray imaging apparatus is an apparatus that may emit X-rays towards an object and acquire images of internal structures of the object using X-rays which have penetrated the object. Since X-rays have different penetration rates depending on the properties of substances constituting an object, images of the internal structures of the object may be produced by detecting the strength or intensity of X-rays penetrating the object.

Imaging technologies using multi-energy X-rays have recently been developed to enhance the contrast between substances constituting an object. X-ray images for different energy bands may be required to acquire a multi-energy image. The X-ray images for each of the different energy bands may be acquired by emitting X-rays of different energy bands from an X-ray source and detecting images of the respective energy bands via an X-ray detector, or by emitting X-rays containing different energy bands once from an X-ray source, detecting the X-rays via an X-ray detector, and separating the X-rays on a per energy band basis.

The latter method of emitting X-rays containing different energy bands once from an X-ray source, detecting the X-rays via an X-ray detector, and separating the X-rays on a per energy band basis, may be preferred in order to minimize an amount of X-ray exposure of an object and prevent a motion artifact due to motion of the object. To apply this method to conventional technologies, the X-ray detector may need to be a Photon Counting Detector (PCD). However, the photon counting detector may require a counting circuit per pixel, which may reduce the yield of a large-area flat-plate type X-ray detector. Moreover, the photon counting detector may need to use a single-crystal light receiving element for generating a pulse in order to discriminate between a single photon, which makes increasing the area of the X-ray detector difficult.

SUMMARY

It is an aspect of an exemplary embodiment to provide an X-ray imaging apparatus, which may detect X-rays via minimal deformation of an existing circuit structure applied to typical electron accumulation without requiring a counting circuit for each pixel, and count photons, thereby producing an X-ray image for each energy band and a multi-energy image, and a control method for the same.

Additional aspects of the exemplary embodiments will be set forth in part in the description which follows and, in part, will be obvious from the description, or may be learned by practice of the exemplary embodiments.

In accordance with one aspect of an exemplary embodiment, an X-ray imaging apparatus includes an X-ray source configured to generate and emit X-rays having a preset broadband, an X-ray detector including a plurality of raw pixels configured to detect an average of ten photons or less when the X-rays are emitted and configured to convert the detected photons into an electrical signal, and an image processor configured to produce a plurality of single-energy images, wherein each of the plurality of singe-energy images respectively corresponds to a plurality of preset energy bands by separating the plurality of raw pixels for each of the plurality of preset energy bands based on the electrical signal, and configured to produce a multi-energy image using the plurality of single-energy images.

The image processor may reconstruct the plurality of raw pixels into a plurality of virtual pixels by grouping the plurality of raw pixels according to a preset number.

The image processor may compare electrical signals of the plurality of raw pixels included in each of the plurality of virtual pixels with reference values corresponding to the respective plurality of preset energy bands in order to separate the plurality of raw pixels for each of the energy bands.

The image processor may count a number of the plurality of raw pixels separated for each of the energy bands.

The image processor may produce the plurality of single-energy images for each of the plurality of preset energy bands by estimating the counted number of raw pixels as a number of photons introduced into each of the plurality of virtual pixels.

In accordance with another aspect of an exemplary embodiment, an X-ray imaging apparatus includes an X-ray source configured to generate and emit X-rays having a preset energy band, an X-ray detector including a plurality of raw pixels configured to detect an average of one photon or less in response to the X-rays which are emitted and convert the detected photons into an electrical signal, and an image processor configured to produce a single-energy image by reconstructing the plurality of raw pixels into a plurality of virtual pixels by grouping the plurality of raw pixels according to a preset number and comparing electrical signals of the plurality of raw pixels included in each of the plurality of virtual pixels with a preset reference value.

The image processor may produce the single-energy image by estimating a number of raw pixels having a greater electrical signal than the preset reference value, among the plurality of raw pixels included in each of the plurality of virtual pixels, as a number of photons introduced into the corresponding virtual pixel.

In accordance with another aspect of an exemplary embodiment, a control method for an X-ray imaging apparatus, includes emitting X-rays having a preset broadband, detecting one photon or less included in the emitted X-rays for each pixel and converting the detected photon into an electrical signal using an X-ray detector including a plurality of raw pixels, separating the plurality of raw pixels for each of a plurality of preset energy bands based on the electrical signal, producing a plurality of single-energy images corresponding to the respective plurality of preset energy bands based on a number of raw pixels separated for each of the plurality of preset energy bands, and producing a multi-energy image using the plurality of single-energy images.

The control method may further include reconstructing the plurality of raw pixels into a plurality of virtual pixels by grouping the plurality of raw pixels according to a preset number.

In accordance with a further aspect of an exemplary embodiment, a control method for an X-ray imaging apparatus, includes generating and emitting X-rays having a preset energy band, detecting ten photons or less included in the X-rays for each pixel and converting the detected photon into an electrical signal using an X-ray detector including a plurality of raw pixels, reconstructing the raw pixels into a plurality of virtual pixels by grouping the raw pixels according to a preset number, and producing a single-energy image by comparing electrical signals of the raw pixels included in each of the virtual pixels with a preset reference value.

BRIEF DESCRIPTION OF THE DRAWINGS

These and/or other aspects of an exemplary embodiment will become apparent and more readily appreciated from the following description of the exemplary embodiments, taken in conjunction with the accompanying drawings of which.

DETAILED DESCRIPTION

Figure 1:
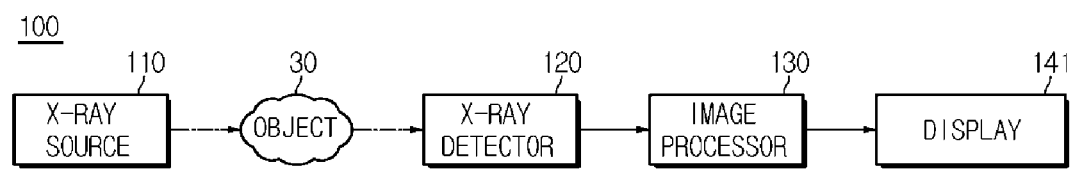
FIG. 1 is a control block diagram of an X-ray imaging apparatus in accordance with an exemplary embodiment.

Reference will now be made in detail to the exemplary embodiments of an X-ray imaging apparatus and a control method thereof, examples of which are illustrated in the accompanying drawings, wherein like reference numerals refer to like elements throughout.

X-ray imaging apparatuses may have different configurations or image capture methods according to body regions to be captured, the kind of X-ray images, image capture purposes, or the like. More specifically, X-ray imaging apparatuses include radiography apparatuses to capture images of the chest, legs, arms, etc., mammography apparatuses to capture images of the breast, fluoroscopy apparatuses to form images of an object on a fluorescent screen, angiography apparatuses, cardiography apparatuses, and the like. An X-ray imaging apparatus in accordance with an exemplary embodiment may be any one of the aforementioned apparatuses, or may be a combination of two or more kinds of X-ray imaging apparatuses.

In addition, an X-ray imaging apparatus in accordance with an exemplary embodiment may be applied to produce a phase contrast X-ray image. The phase contrast X-ray image is produced as X-rays undergo a phase shift due to refraction and interference by substances constituting an object while penetrating the object. The phase contrast X-ray image may be produced using X-ray images for two or more different energy bands.

Figure 2A:
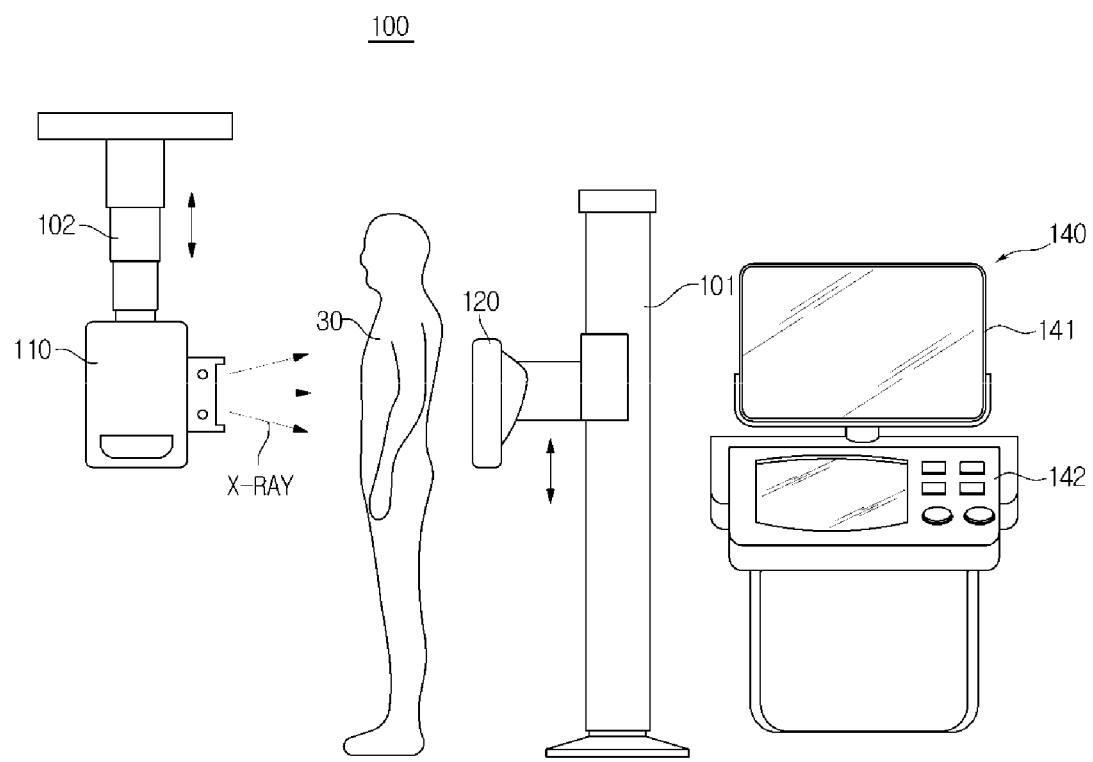
FIG. 2A is a view showing an external appearance of the X-ray imaging apparatus in the form of a radiography apparatus in accordance with an exemplary embodiment.
Figure 2B:
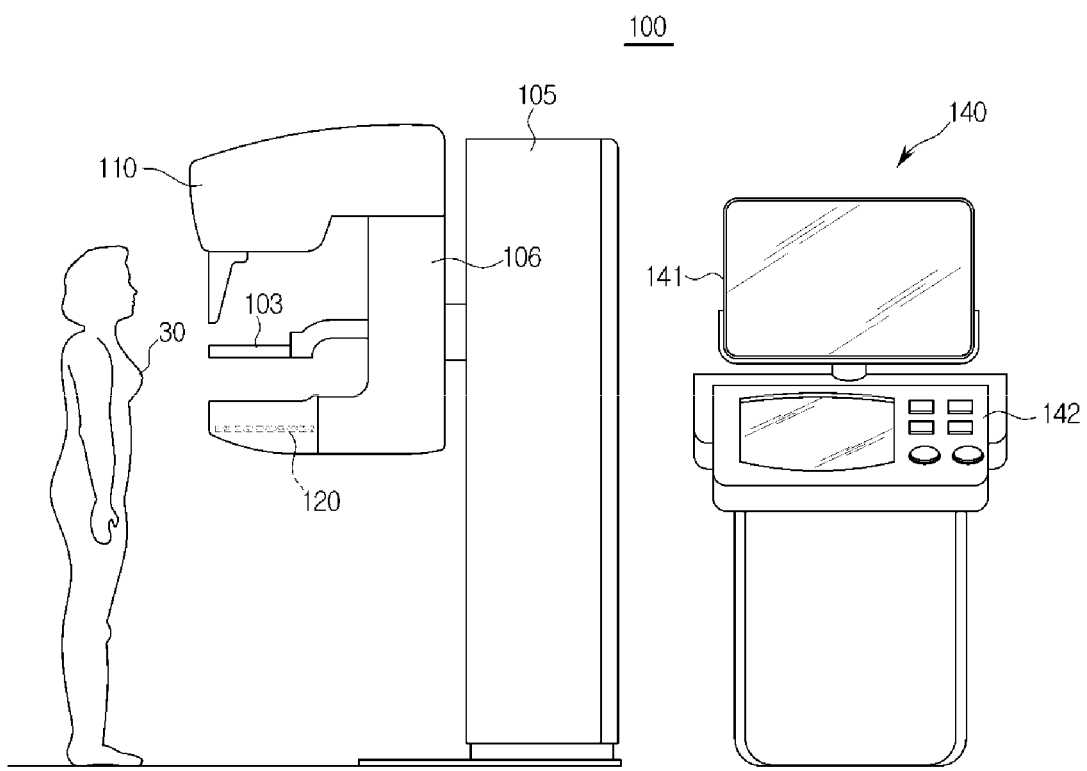
FIG. 2B is a view showing an external appearance of the X-ray imaging apparatus in the form of a mammography apparatus in accordance with an exemplary embodiment.

FIG. 1 is a control block diagram of an X-ray imaging apparatus in accordance with an exemplary embodiment, FIG. 2A is a view showing an external appearance of an X-ray imaging apparatus in the form of a radiography apparatus in accordance with an exemplary embodiment, and FIG. 2B is a view showing an external appearance of an X-ray imaging apparatus in the form of a mammography apparatus in accordance with an exemplary embodiment.

Referring to FIG. 1, the X-ray imaging apparatus 100 in accordance with an exemplary embodiment includes an X-ray source 110 to generate X-rays and emit X-rays towards an object 30, an X-ray detector 120 to detect X-rays which have penetrated the object 30 and convert the X-rays into an electrical signal, an image processor 130 to count photons introduced into the X-ray detector 120 for a plurality of different energy bands based on the electrical signal converted by the X-ray detector 120 and produce an X-ray image of the object, and a display 141 to display the X-ray image of the object.

The X-ray source 110 emits broadband X-rays containing a plurality of different energy bands. The X-ray detector 120 has a two-dimensional (2D) array of pixels. The pixels have a small size so as to enable detection of a minimum number of photons for each pixel when the X-ray source 110 emits X-rays once.

In an exemplary embodiment, a plurality of energy bands refers to different energy bands, and different energy bands refer to energy bands having different upper limits and/or different lower limits.

In addition, in an exemplary embodiment, a broadband is relative to an energy band separated by the image processor 130 that will be described hereinafter. Herein, a broadband is referred to as including a plurality of energy bands and each of the plurality of energy bands correspond to a single-energy image.

The image processor 130 compares an electrical signal output from each pixel of the X-ray detector 120 with a reference value corresponding to each energy band, thereby separating the pixels constituting the X-ray detector 120 on a per energy band basis. Single-energy images for energy band may be acquired using the pixels separated per energy band, and a multi-energy image may be produced using the single-energy images per energy band.

The display 141 may display the produced multi-energy image, and may also display the single-energy images as needed.

Referring to FIGS. 2A and 2B an object 30 is located between the X-ray source 110 and the X-ray detector 120. The object shown in FIG. 2A is a human chest, and the object shown in FIG. 2b is a human breast, however, an object is not limited to these examples. The X-ray detector 120 detects X-rays having penetrated the object 30 when the X-ray source 110 emits X-rays toward the object 30.

The X-ray imaging apparatus 100 includes a host device 140 to provide a user interface. The host device 140 may include the display 141 to display X-ray images and an inputter 142 to receive an instruction from a user. In an exemplary embodiment, the user may be a person who diagnoses a subject using the X-ray imaging apparatus 100, such as a doctor, radiotherapist, nurse, etc., but is not limited thereto, and all people who use the X-ray imaging apparatus 100 are within the scope of a user.

In an exemplary embodiment, the object is an inspection region of a subject, such as a patient, to be diagnosed using the X-ray imaging apparatus 100, i.e. an X-ray image capture region. The subject may be a living organism, such as a human or animal, but is not limited thereto. All things, the internal structures of which are to be imaged by the X-ray imaging apparatus 100, are within the scope of the subject.

Assuming that the X-ray imaging apparatus 100 is a radiography apparatus, as exemplarily shown in FIG. 2A, the X-ray source 110 and the X-ray detector 120 are moved to a position corresponding to the object 30. In the X-ray imaging apparatus 100, in order to capture an image of the object 30 included in the subject who is standing or sitting, the X-ray source 110 may be mounted to a holder 102 that is connected to a ceiling in a length adjustable manner and the X-ray detector 120 may be mounted to a support stand 101 in a vertically movable manner. Alternatively, the X-ray detector 120 may be mounted in a table, on which the subject lies, to move in a longitudinal direction of the table and the X-ray source 110 may be mounted to a ceiling to move in a longitudinal direction of the table.

Assuming that the X-ray imaging apparatus 100 is a mammography apparatus, as exemplarily shown in FIG. 2B, the breast is the object 30 which is placed on the X-ray detector 120 and then X-rays are emitted toward the object 30 from above. In this case, in order to acquire a vivid X-ray image of the breast, the breast 30 is compressed using a compression paddle 103. The compression paddle 103 may be mounted to a frame 106 in a vertically movable manner.

The X-ray source 110 and the X-ray detector 120 are connected to the frame 106, and the frame 106 is connected to a gantry 105. In this case, the frame 106 is movable in a longitudinal direction of the gantry 105 to a position corresponding to the object 30.

As described above, the X-ray imaging apparatus 100 forms images of internal structures of the object 30 using different X-ray attenuations of substances constituting the object 30. An attenuation coefficient numerically represents X-ray attenuation per substance. The attenuation coefficient may be represented by the following Equation 1.

$$I=I_0*\exp(-\mu(E)T) \quad \text{Equation 1}$$

Here, $I_0$ is the intensity of X-rays emitted to the object, I is the intensity of X-rays having penetrated the object, and $\mu(E)$ is an attenuation coefficient of a substance related to X-rays having energy E. T is a thickness of the substance through which the X-rays penetrate. It will be appreciated from Equation 1 that the intensity of X-rays having penetrated a substance decreases as an attenuation coefficient of the substance increases.

Figure 3A:
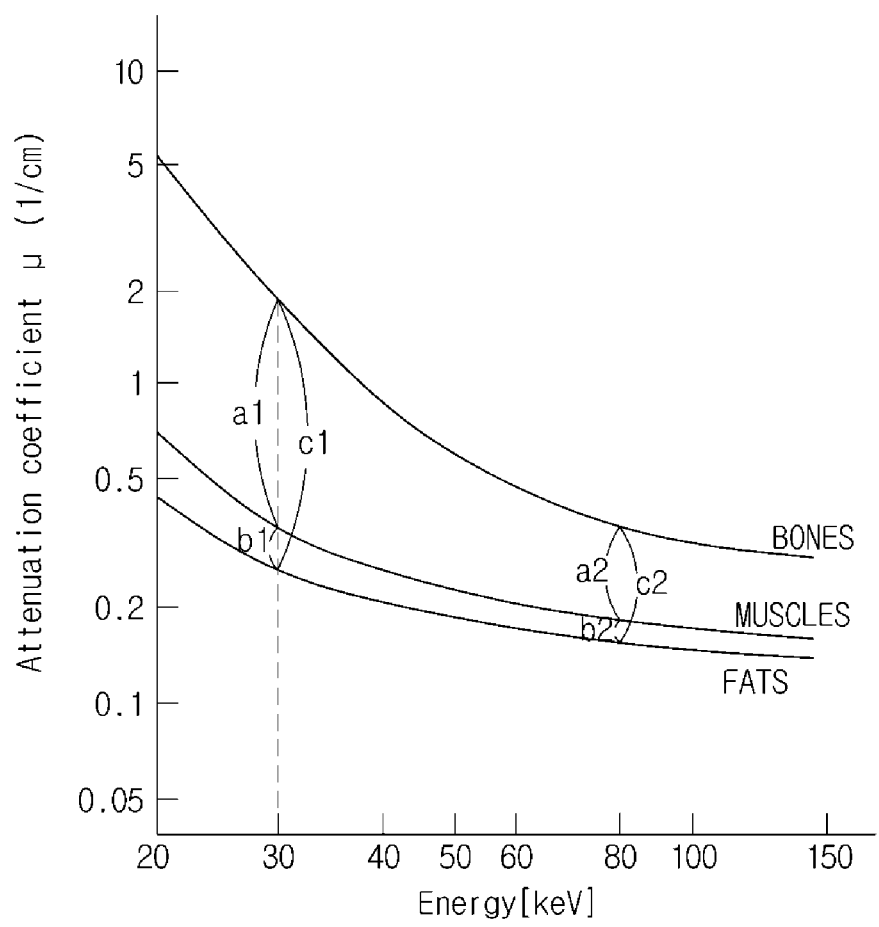
FIG. 3A is a graph showing attenuation coefficients of bones, muscles, and fats in accordance with an exemplary embodiment.
Figure 3B:
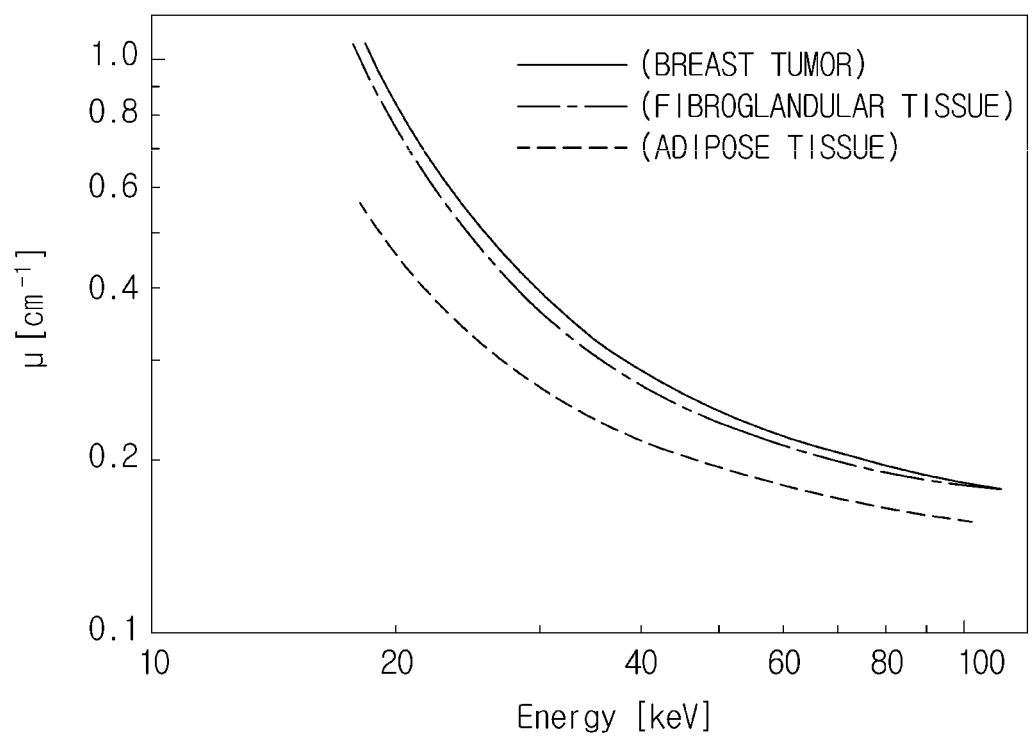
FIG. 3B is a graph showing attenuation coefficients of soft tissues constituting the breast in accordance with an exemplary embodiment.

FIG. 3A is a graph showing attenuation coefficients of bones, muscles, and fats in accordance with an exemplary embodiment, and FIG. 3B is a graph showing attenuation coefficients of soft tissues constituting the breast in accordance with an exemplary embodiment.

Referring to FIG. 3A, a curve representing an attenuation coefficient of bones is located above curves representing attenuation coefficients of soft tissues (muscles and fats). This means that an X-ray penetration rate of soft tissues is greater than an X-ray penetration rate of bones. In addition, when comparing a curve representing an attenuation coefficient of muscles with a curve representing an attenuation coefficient of fats, it will be appreciated that an X-ray penetration rate of muscles is less than an X-ray penetration rate of fats.

In addition, it will be appreciated that a difference between attenuation coefficients varies based on the level of energy. In one example, a difference a1 between the attenuation coefficient of bones and the attenuation coefficient of muscles when X-ray energy corresponds to 30 keV is greater than a difference a2 between the attenuation coefficient of bones and the attenuation coefficient of muscles when X-ray energy corresponds to 80 keV. That is, a difference between the attenuation coefficients of bones and muscles increases as X-ray energy decreases.

Differences c1, c2 between the attenuation rates of bones and fats exhibit the same results. Likewise, differences b1, b2 between the attenuation rates of muscles and fats increase towards a lower energy band, although the differences are not great.

Referring to FIG. 3B, in the case of soft tissues constituting the breast, likewise, it will be appreciated that differences between attenuation coefficients of breast tumors, fibroglandular tissues, and adipose tissues vary, and these differences between the attenuation coefficients increase towards a lower energy band.

To attain an X-ray image having enhanced contrast between substances constituting an object, the X-ray imaging apparatus 100 may utilize variations in differences between attenuation coefficients of substances depending on X-ray energy. More specifically, X-ray images corresponding to a plurality of different energy bands may be acquired, and separation of the substances which make up an object or production of a more vivid X-ray image of a specific substance of the substances which make up the object may be accomplished using the acquired X-ray images.

In a detailed example, a high-energy image and a low-energy image of an object may be acquired, and appropriate weighting values may be added and then subtracted from the high-energy image and the low-energy image respectively, to produce a bone image from which soft tissues are removed or subtracted, or a soft tissue image from which bones are removed or subtracted.

In an exemplary embodiment, the aforementioned X-ray image is referred to as a multi-energy image, and an X-ray image corresponding to each energy band is referred to as a single-energy image.

To produce a multi-energy image, first, an X-ray image per energy band is acquired. The single-energy image per energy band may be acquired by emitting X-rays of different energy bands respectively from an X-ray source, or by emitting X-rays containing different energy bands once from an X-ray source, detecting the X-rays using an X-ray detector, and separating the detected X-rays on a per energy band basis.

The X-ray imaging apparatus 100 employs the latter method, in order to minimize X-ray exposure of the object 30 and loading of the X-ray source 110 and to attain a high-resolution multi-energy image.

Hereinafter, operation of respective components of the X-ray imaging apparatus 100 will be described in detail.

Figure 4:
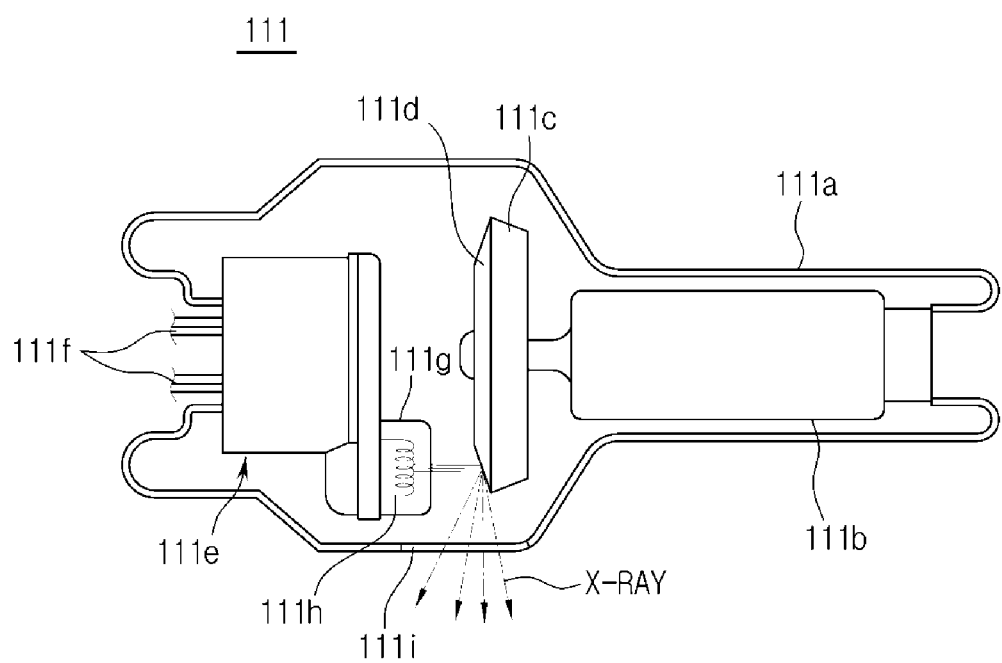
FIG. 4 is a view schematically showing a configuration of an X-ray tube in accordance with an exemplary embodiment.

FIG. 4 is a view schematically showing a configuration of an X-ray tube in accordance with an exemplary embodiment.

The X-ray source 110 includes an X-ray tube 111 to generate X-rays. Referring to FIG. 4, the X-ray tube 111 may be embodied as a diode vacuum tube including an anode 111c and a cathode 111e. A tube body may be a glass tube 111a formed of hard silicate glass, for example.

The cathode 111e includes a filament 111h and a focusing electrode 111g for focusing electrons. The focusing electrode 111g is also called a focusing cup. The interior of the glass tube 111a is evacuated to a pressure of about 10 mmHg, and the filament 111h of the cathode 111e is heated to a high temperature to generate thermal electrons.

In one example, the filament 111h may be a tungsten filament, and may be heated as current is applied to an electrically conductive wire 111f connected to the filament 111h. Note that the exemplary embodiment is not limited to provide the cathode 111e with the filament 111h, and a carbon nano-tube that can be driven at high pulses may be employed as the cathode.

The anode 111c may be formed of copper. A target material 111d may be applied to or disposed on one side of the anode 111c facing the cathode 111e. The target material 111d may be a high resistance material, such as chromium (Cr), iron (Fe), cobalt (Co), nickel (Ni), tungsten (W), molybdenum (Mo), etc. As the melting point of the target material 111d increases, the size of a focal spot decreases.

When a high voltage is applied between the cathode 111e and the anode 111c, thermal electrons are accelerated and collide with the target material 111g of the anode 111c, and X-rays are generated. The generated X-rays are emitted outward through a window 111i. The window 111i may be formed of a thin beryllium (Be) film. In this case, a filter may be located at the front side or the rear side of the window 111i so as to filter X-rays having a specific energy band.

The target material 111d may be rotated by a rotor 111b. If the target material 111d is rotated, a heat accumulation rate may be increased by ten times or more on a per unit area basis and the size of the focal spot may be reduced as compared to the case in which the target material 111d is stationary.

The voltage applied between the anode 111c and the cathode 111e of the X-ray tube 111 is referred to as a tube voltage, and the magnitude of the tube voltage may be represented as a peak value (kVp). If the tube voltage increases, the velocity of thermal electrons increases, and consequently the energy level of X-rays (the energy level of photons) generated via collision between the thermal electrons and the target material increases. A current applied to the X-ray tube 111 is referred to as tube current, and the magnitude of the tube current may be represented as an average value (mA). When the tube current increases, the flux of X-rays (the number of X-ray photons) increases.

Accordingly, the energy level of X-rays may be controlled based on the tube voltage, and the intensity or flux of X-rays may be controlled based on tube current and X-ray exposure time. The energy level and strength of X-rays may be controlled based on the kind or properties of the object 30.

X-rays emitted from the X-ray source 110 have a given energy band and may be defined by upper and lower limits of the energy band. The upper limit of the energy band, i.e. the maximum energy of X-rays, may be adjusted based on the magnitude of tube voltage, and the lower limit of the energy band, i.e. the minimum energy of X-rays, may be adjusted by a filter of the X-ray source 110. When X-rays of a low energy band is filtered using the filter, the average energy of X-rays may be increased. The energy of X-rays may be represented by the maximum energy or the average energy.

Figure 5A:
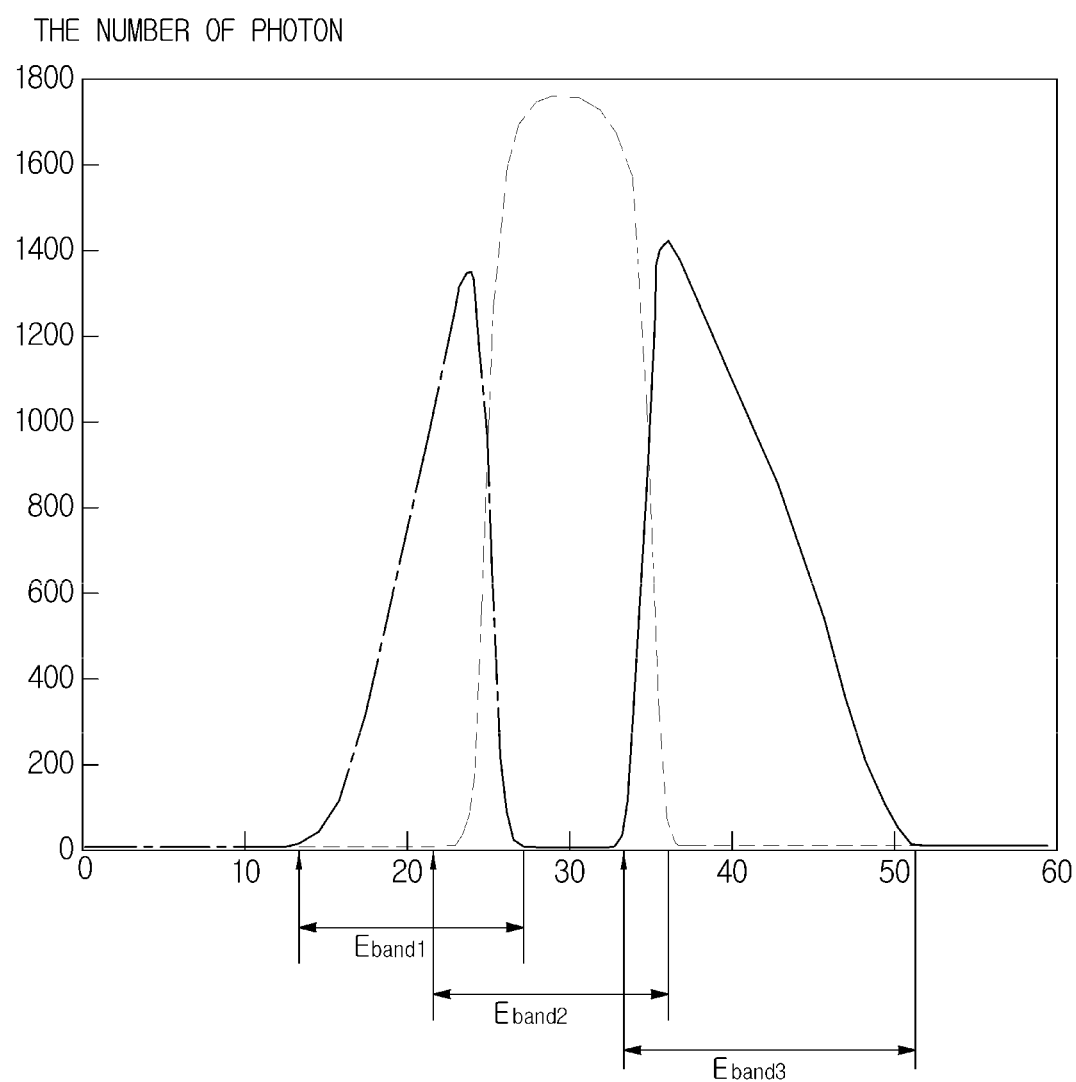
FIG. 5A is a graph showing energy bands corresponding to a plurality of single-energy images in accordance with an exemplary embodiment.
Figure 5B:
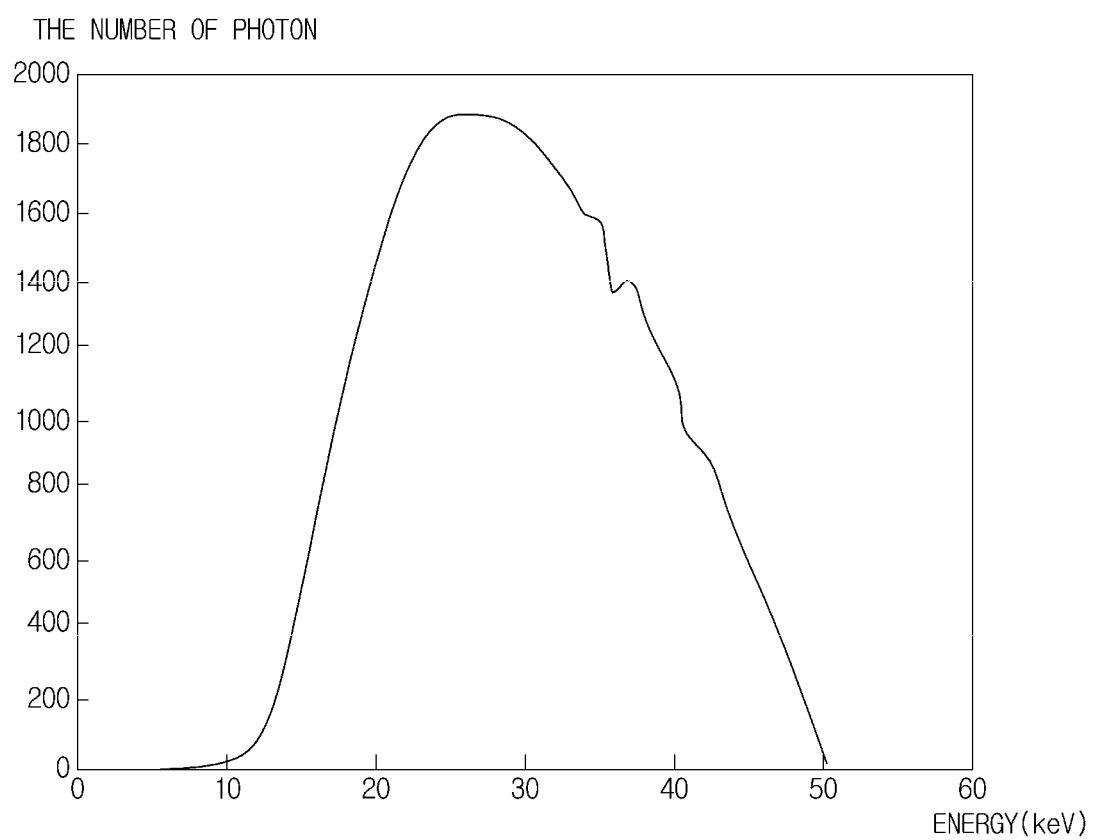
FIG. 5B is a graph showing energy bands of X-rays emitted from an X-ray source in accordance with an exemplary embodiment.

FIG. 5A is a graph showing energy bands corresponding to a plurality of single-energy images to be acquired in accordance with an exemplary embodiment, and FIG. 5B is a graph showing energy bands of X-rays emitted from the X-ray source in accordance with an exemplary embodiment.

In one example, when the object 30 is the breast, in order to produce a multi-energy image, the X-ray imaging apparatus 100 may acquire single-energy images corresponding to three different energy bands $E_{band1}$, $E_{band2}$, $E_{band3}$ as exemplarily shown in FIG. 5A.

To this end, as exemplarily shown in FIG. 5B, the X-ray source 110 may emit X-rays containing the three different energy bands. That is, energy of X-rays emitted from the X-ray source 110 may have an upper limit of 50 keV and a lower limit of 10 keV. In a detailed example, the tube voltage of the X-ray tube 111 may be set to 50 kVp for generation of X-rays, and X-rays having a low energy band (about 0~10 keV) may be filtered.

Figure 6:
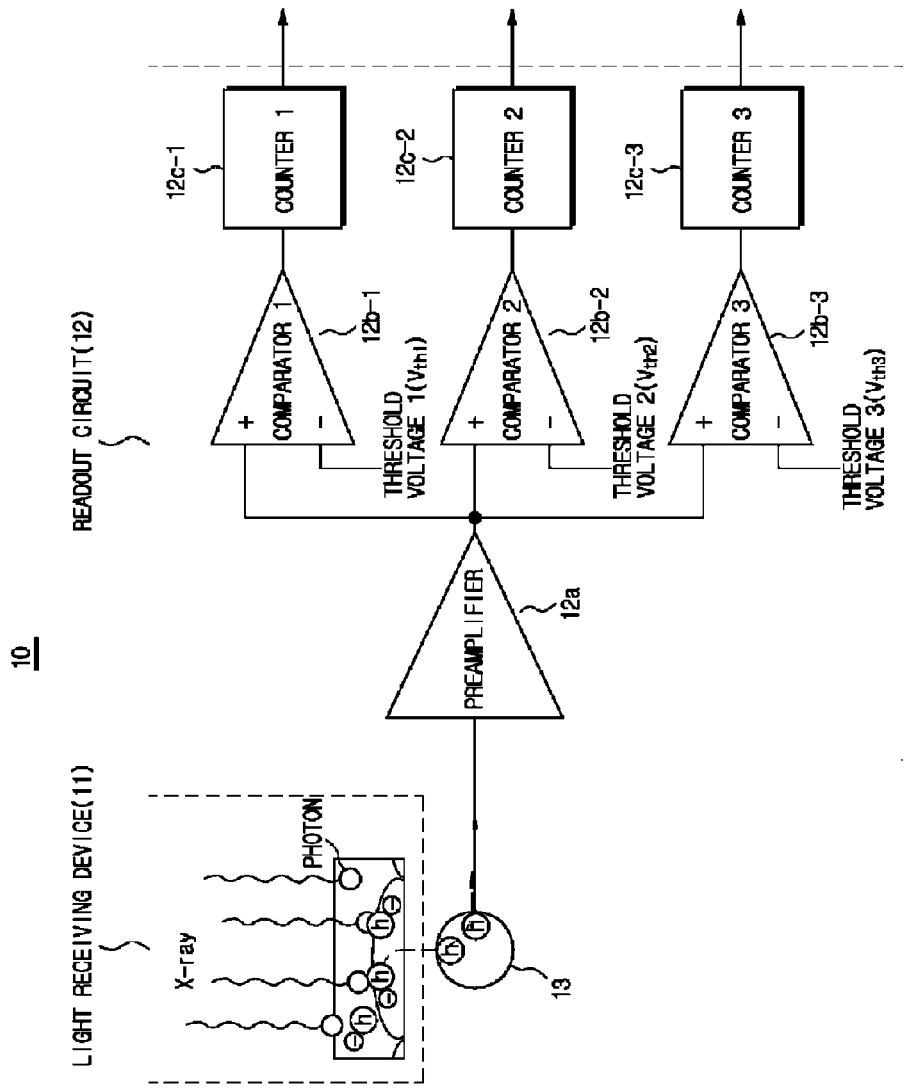
FIG. 6 is a view schematically showing a circuit configuration of a single pixel of a typical photon counting type X-ray detector.

FIG. 6 is a view schematically showing a circuit configuration of a single pixel of a typical photon counting type X-ray detector.

Conventionally, in order to separate X-rays emitted from an X-ray source on a per energy band basis, a photon counting type X-ray detector including a plurality of pixels 10 as exemplarily shown in FIG. 6 has been used. For example, in order to separate X-rays for three energy bands as exemplarily shown in FIG. 5A, the single pixel 10 includes three comparator circuits. More specifically, when electrons or holes generated in a light receiving device 11 using a single photon are output as a voltage signal by way of a pre-amplifier 12a of a readout circuit 12, which is connected to the light receiving device 11 via a bump bond 13, the voltage signal is input to three comparators 12b-1, 12b-2, 12b-3.

Then, when threshold voltage 1 $V_{th1}$ to threshold voltage 3 $V_{th3}$ are input to the respective comparators, the comparator 1 12b-1 compares the threshold voltage 1 with the input voltage, and a counter 1 12c-1 counts the number of photons that generate a voltage greater than the threshold voltage 1. In the same manner, a counter 2 12c-2 counts the number of photons that generate a voltage greater than the threshold voltage 2, and a counter 3 12c-3 counts the number of photons that generate voltage greater than the threshold voltage 3.

As described above, the photon counting type X-ray detector may require a counting circuit per pixel, which causes a complicated pixel circuit and a low yield. Moreover, it may be necessary to utilize a single-crystal photoconductor as the light receiving device, which makes realization of a large-area X-ray detector difficult.

In the X-ray detector 120 of the X-ray imaging apparatus 100 according to exemplary embodiment, instead of including a counting circuit per pixel, a charge integration mode is adopted in which charges introduced into a single pixel for a given time are accumulated and thereafter, an electrical signal is acquired from the accumulated charges. Thus, realization of the X-ray detector 120 having a large area may be possible.

Figure 7:
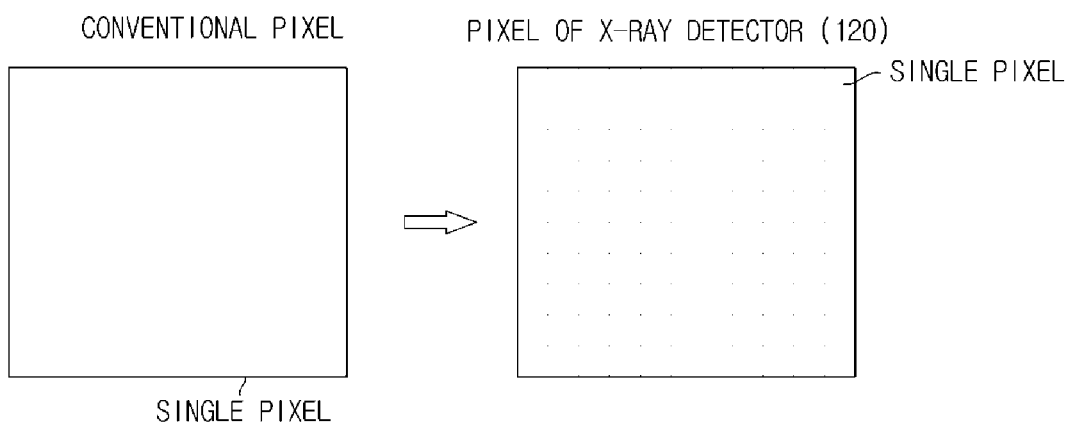
FIG. 7 is a view schematically showing the size of pixels of an X-ray detector.
Figure 8:
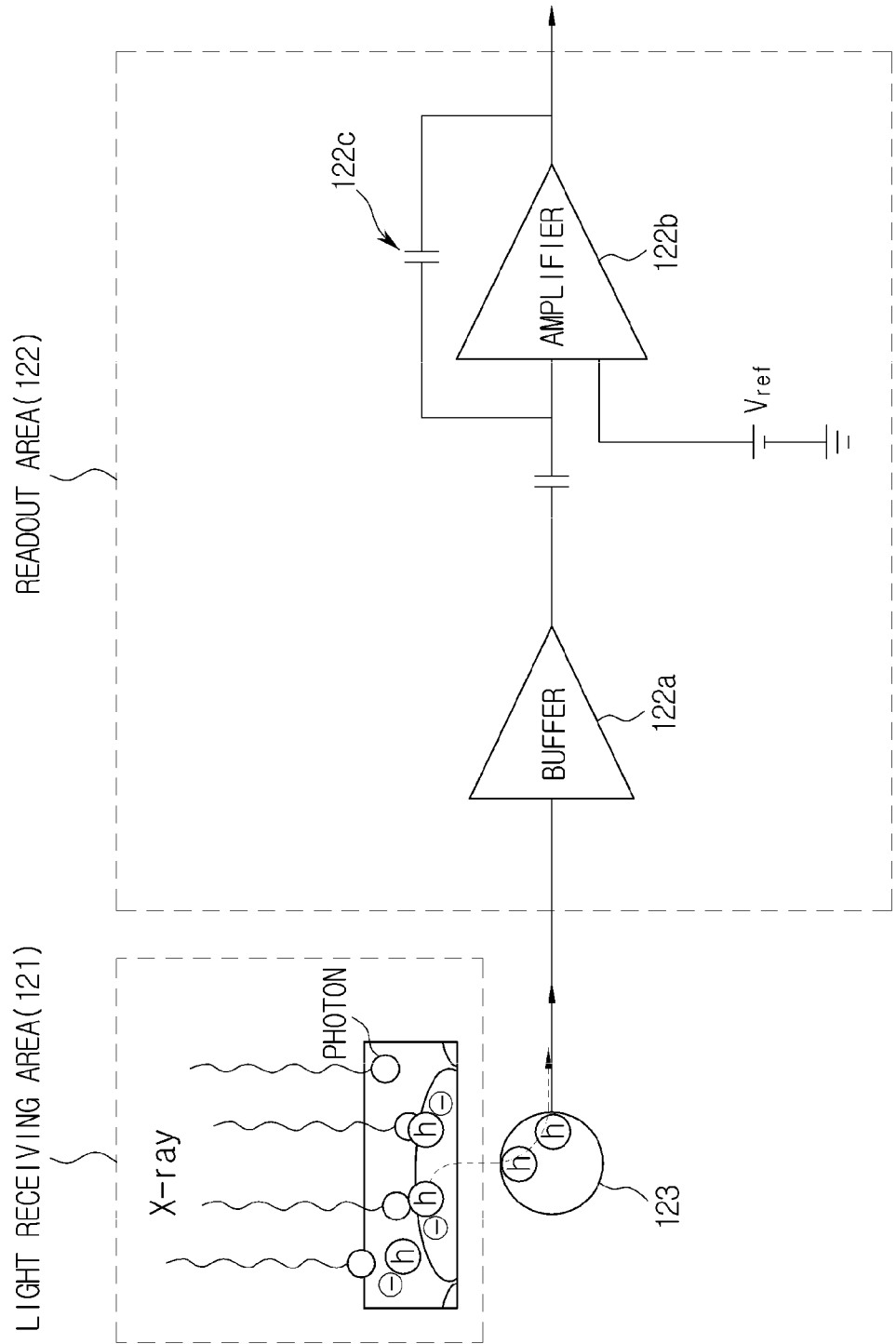
FIG. 8 is a view schematically showing a circuit configuration of a single pixel of the X-ray detector in accordance with an exemplary embodiment.

FIG. 7 is a view schematically showing the size of pixels of the X-ray detector included in the X-ray imaging apparatus in accordance with an exemplary embodiment, and FIG. 8 is a view schematically showing a circuit configuration of a single pixel of the X-ray detector included in the X-ray imaging apparatus in accordance with an exemplary embodiment.

In order to count photons of X-rays having penetrated an object on a per energy band basis using the charge integration type X-ray detector 120, as described above, a single pixel of the X-ray detector 120 may be configured to have a small size and a low flux of X-rays in order to detect a minimum number of photons, e.g., ten photons or less on average.

That is, when calculating the average number of photons detected by all pixels constituting the X-ray detector 120, the number of photons detected for each pixel may be ten photons or less. When ten photons or less are detected per pixel, the X-ray imaging apparatus 100 may implement reliable image processing under the assumption of a signal output from each pixel of the X-ray detector 120 corresponding to a single photon.

The size of the pixels and the flux of the X-rays (X-ray exposure time and tube current) may be equal to or less than reference values that are experimentally, theoretically or statistically determined in consideration of interrelations therebetween.

In a more detailed example, a single pixel of the X-ray detector 120 may be designed to detect, on average, one photon or less. When one photon or less on average is detected per pixel, the X-ray imaging apparatus 100 may achieve enhanced reliability with regard to the implementation of the image processing. The image processing is implemented under the assumption that a signal output from each pixel of the X-ray detector 120 corresponds to a single photon.

In one example, as exemplarily shown on the left of FIG. 7, when a conventional X-ray detector has a pixel size of 55 µm, the X-ray detector 120 of the X-ray imaging apparatus 100 may have a pixel size of 5 µm as exemplarily shown in the right of FIG. 7. That is, the pixel size may be 5 µm in length and width respectively.

Referring to FIG. 8, in one example, the X-ray detector 120 may include a light receiving area 121 to detect X-rays and convert the X-rays into charges, and a readout area 122 to read out the amount of charges and output a readout value as an electrical signal.

Referring to FIG. 8, when photons of X-rays are introduced into the light receiving area 121, electrons in a valence band receive energy of the photons and are excited to a conduction band beyond a band gap energy difference. This results in the generation of electron-hole pairs in a depletion region, and the electrons or holes generated in the depletion region move to the readout area 122 when bias is applied to the light receiving area 121. The light receiving area 121 may include PN photodiodes, PIN photodiodes, Schottky photodiodes, avalanche photodiodes, etc.

The readout area 122 may take the form of a 2D pixel array and may read out an electrical signal using a readout circuit per pixel. The readout area 122, as exemplarily shown in FIG. 8, is a readout area of a single pixel. In addition, the X-ray detector 122 may include active pixels having a circuit configuration to amplify an electrical signal in each pixel, and thus may read out a small electrical signal generated from a single photon.

The flow of charges 123, input from the light receiving area 121, is stored in a buffer 122a for a given time, and then is output as a voltage signal to be input to an amplifier 122b. The output voltage signal is amplified to a given magnitude by the amplifier 122b. Since one photon or less is input to the single pixel of the X-ray detector 120, the voltage signal output from the amplifier 122b may be estimated as a voltage signal of a single photon.

An amplification rate of an electrical signal is referred to as gain, and a gain of the X-ray detector 120 is referred to as detection sensitivity. The gain of the amplifier 122b may vary based on the capacity of a capacitor 122c. In order to record an electrical signal generated by a single photon without loss, the X-ray detector 120 may require a sufficiently high detection sensitivity. When the X-ray detector 120 has a single pixel configuration as exemplarily shown in FIG. 8, the capacitor 122c may have a capacity to enhance the detection sensitivity sufficient so as to record an electrical signal generated by a single photon without loss. The capacity of the capacitor 122c may also be experimentally, statistically or theoretically determined.

In addition, the X-ray detector 120 may have a pixel pitch of several micrometers or less to minimize loss of an electrical signal generated by a photon, and may limit a flux of X-rays per pixel by adjusting the tube voltage and X-ray exposure time of the X-ray source 110.

In addition, it may be possible to limit the number of photons introduced into each pixel by reducing an exposure time interval of X-rays. To this end, the X-ray detector 120 may be configured to acquire an image frame within a short period of time. Thus, the X-ray detector 120 may be a detector that enables high-speed readout. In a detailed example, when using a Thin Film Transistor (TFT) formed of oxides rather than amorphous silicon, mobility of electrons is increased which enables high-speed driving of the X-ray detector 120.

In another example, when the X-ray detector 120 is a Complementary Metal Oxide Semiconductor (CMOS) detector, the X-ray detector 120 may achieve a remarkably enhanced readout speed. Thus, in the mammography apparatus, a frame rate of 20 fps or more may be realized.

Meanwhile, the X-ray detector 120 may adopt indirect conversion in which X-rays emitted from the X-ray source 110 are converted into visible light using a thin film shaped gadolinium oxysulfide (GADOX) scintillator, or a micro column type or needle type cesium iodide (CSI (TI)) scintillator. The visible light is then converted into an electrical signal using an amorphous silicon (a-Si) photodiode as a light receiving device.

Alternatively, the X-ray detector 120 may adopt direct conversion in which a photoconductor, such as amorphous selenium (a-Se), cadmium zinc telluride (CdZnTe), mercury (II) iodide ($HgI_2$), lead (II) iodide ($PbI_2$), etc., is used as a light receiving device to directly convert X-rays emitted from the X-ray source 110 into an electrical signal.

Figure 9:
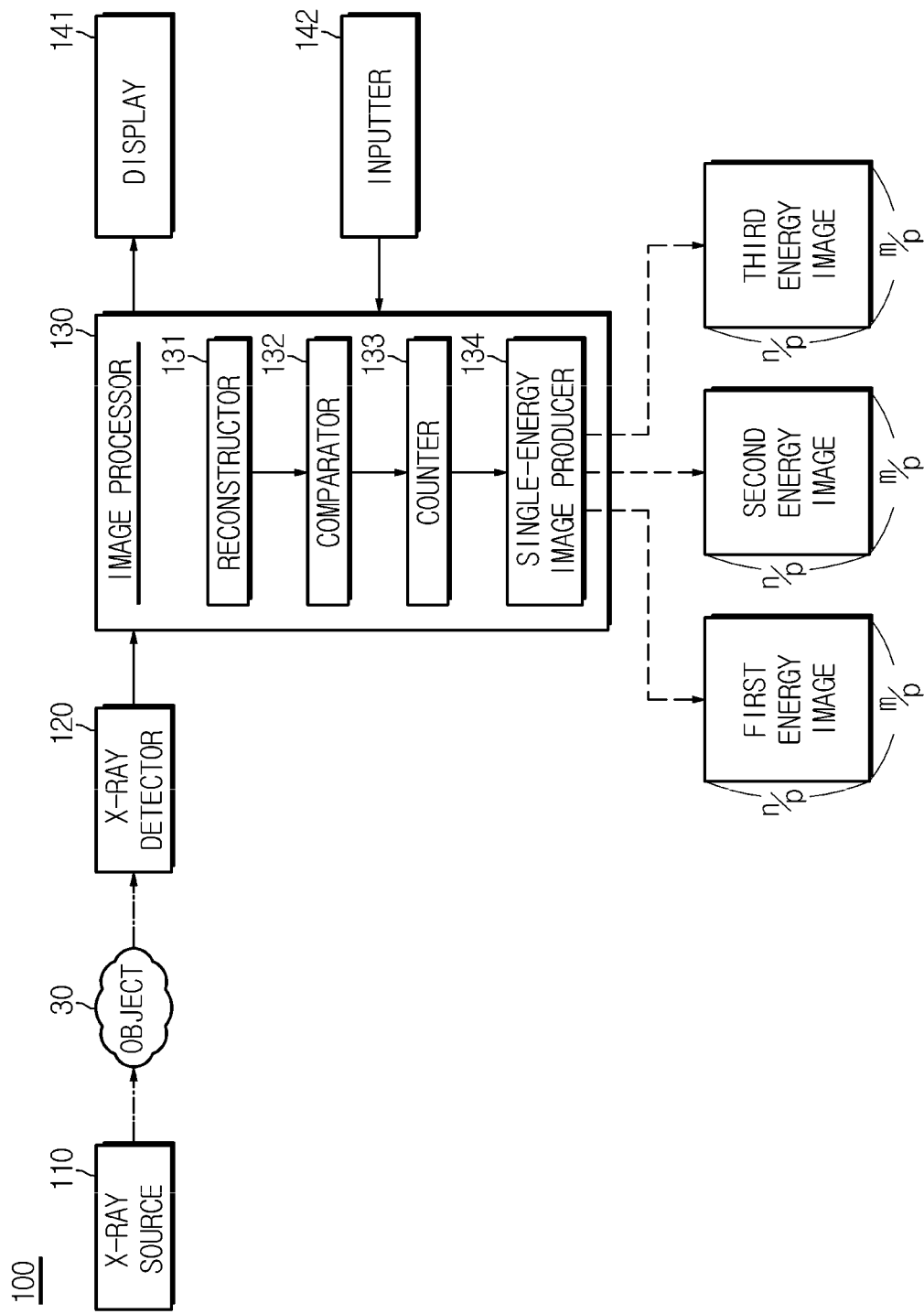
FIG. 9 is a control block diagram showing a detailed configuration of an image processor included in the X-ray imaging apparatus in accordance with an exemplary embodiment.

FIG. 9 is a control block diagram showing a detailed configuration of the image processor included in the X-ray imaging apparatus in accordance with an exemplary embodiment.

Referring to FIG. 9, the image processor 130 includes a reconstructor 131 to reconstruct the pixels constituting the X-ray detector 120 into a plurality of virtual pixels by grouping the pixels, a comparator 132 to separate the pixels on a per energy band basis by comparing an electrical signal of each pixel with a preset reference value, a counter 133 to count the number of separated pixels per energy band, and a single-energy image producer 134 to produce a single-energy image per energy band.

The number of pixels to be reconstructed into a single virtual pixel may be selected by the user. The X-ray imaging apparatus 100 may further include the inputter 142 to receive an instruction, related to the number of pixels to be reconstructed into a single virtual pixel, from the user.

In order to distinguish between pixels constituting the X-ray detector 120 from virtual pixels reconstructed by the image processor 130, in the following description of the exemplary embodiment, the pixels of the X-ray detector 120 are referred to as raw pixels.

The X-ray detector 120 transmits an electrical signal acquired for each raw pixel to the image processor 130. In this case, the X-ray detector 120 includes an Analog to Digital Converter (ADC) to convert the electrical signal into a digital signal, and thus transmits the digital signal.

Image data is transmitted from the X-ray detector 120 to the image processor 130. The image data is a set of raw pixel data, and the raw pixel data contains information regarding the electrical signal converted in a corresponding raw pixel. In addition, the raw pixel data may contain position information of a corresponding raw pixel according to the format of the image data.

Hereinafter, the operation of the image processor will be described in detail with reference to FIGS. 10A and 10B and FIG. 11 in accordance with an exemplary embodiment.

A raw pixel has a small size so that one photon or less can be introduced. Thus, the reconstructor 131 may reconstruct a plurality of raw pixels into a plurality of virtual pixels by grouping the pixels.

Figure 10A:
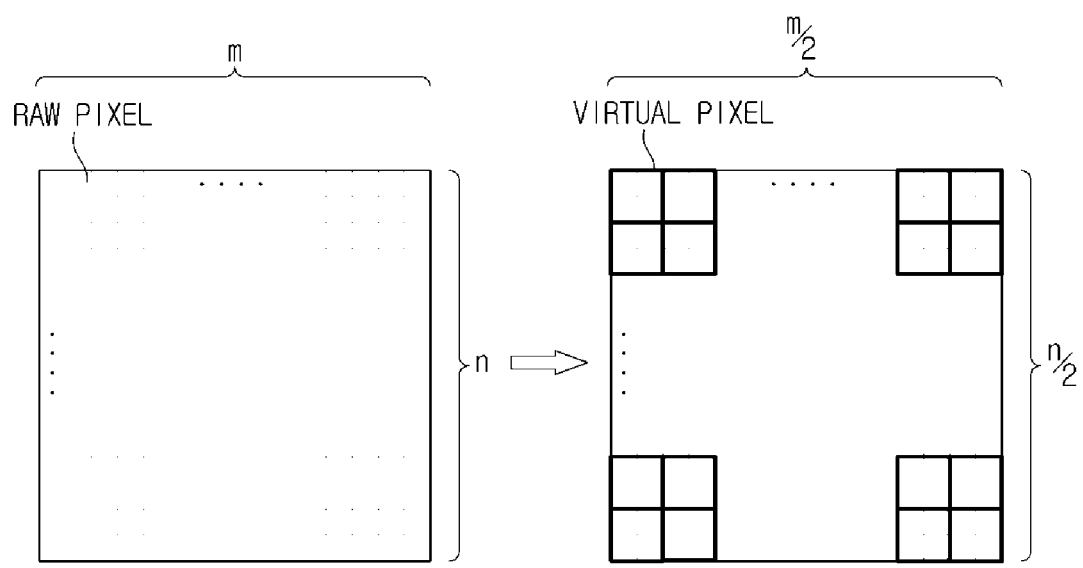
FIGS. 10A and 10B are views schematically showing the size of reconstructed virtual pixels in accordance with an exemplary embodiment.
Figure 10B:
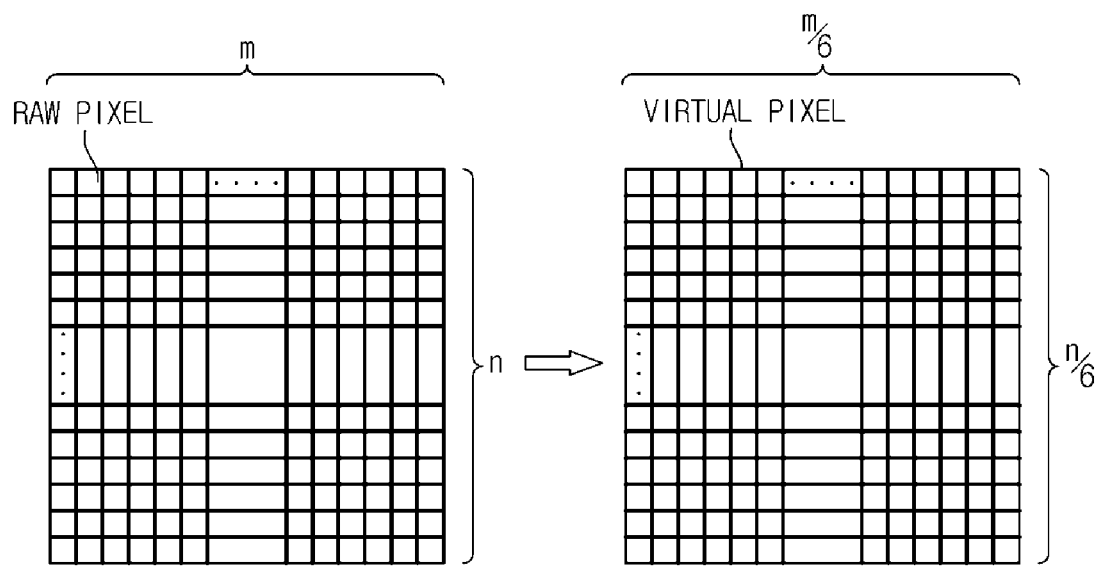

FIGS. 10A and 10B are views schematically showing the size of reconstructed virtual pixels in accordance with an exemplary embodiment.

As exemplarily shown in FIG. 10A, when the raw pixels of the X-ray detector 120 are arranged into a 2D array of m×n (here, m and n are integers of 2 or more and may be equal), the reconstructor 131 may group the raw pixels of m×n into a unit of 2×2 to reconstruct virtual pixels of m/2×n/2. In this case, the image processor 130 recognizes that image data transmitted from the X-ray detector 120 has an array of m/2×n/2.

In another example, as exemplarily shown in FIG. 10B, the reconstructor 131 may group the raw pixels of m×n into a unit of 6×6 to reconstruct virtual pixels of m/6×n/6. In this case, the image processor 130 recognizes that image data transmitted from the X-ray detector 120 has an array of m/6×n/6.

FIGS. 10A and 10B are given by way of example to schematically explain the operation of the reconstructor 131, and the number of raw pixels constituting a single virtual pixel is not limited to these examples. The number of raw pixels constituting a single virtual pixel may be set by the image processor 130, or may be set by the user via the inputter 142 as described above.

Figure 11:
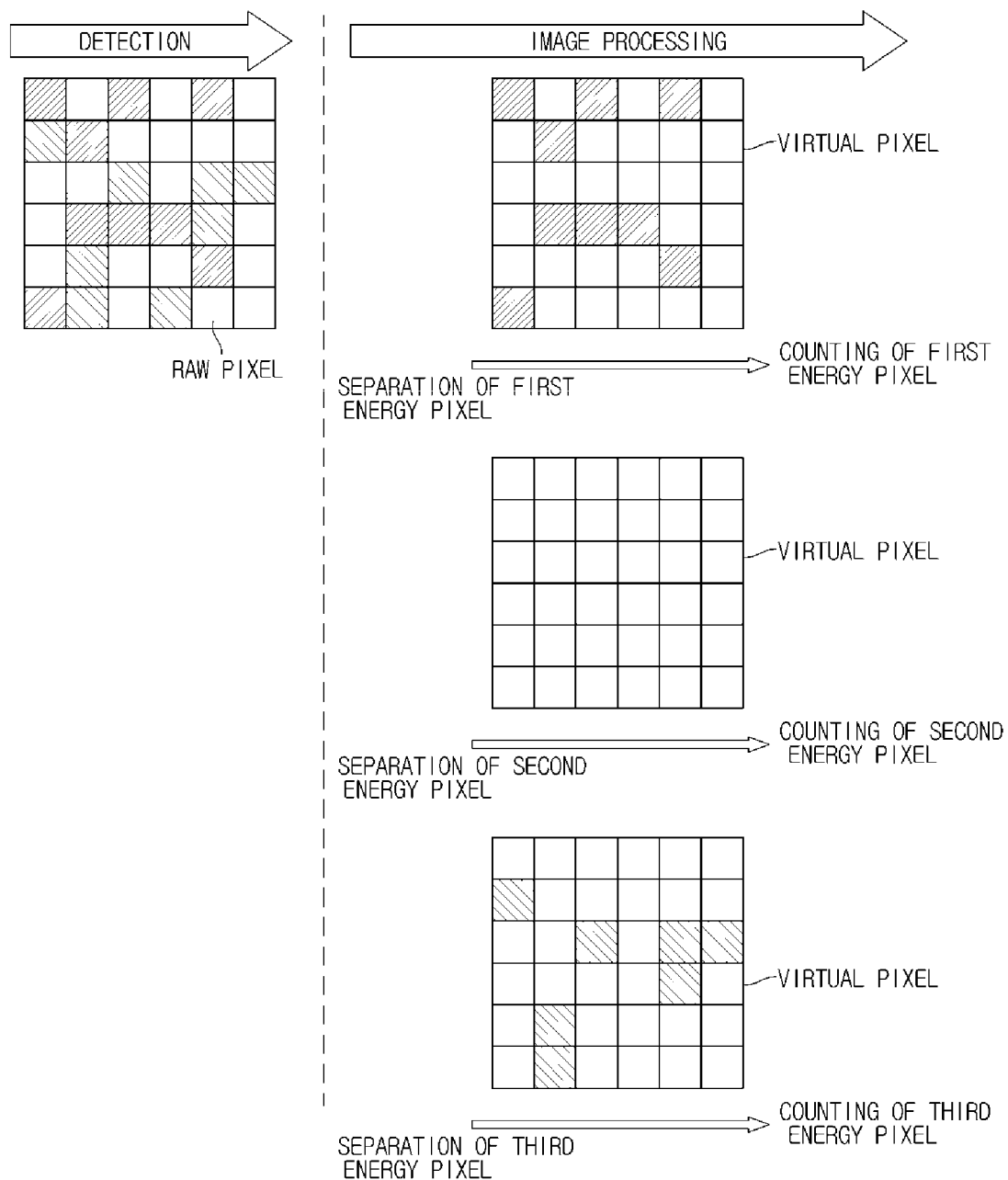
FIG. 11 is a view schematically showing the separation of raw pixels, constituting a single virtual pixel, per energy band in a comparator in accordance with an exemplary embodiment.

FIG. 11 is a view schematically showing the separation of raw pixels, constituting a single virtual pixel, per energy band in a comparator in accordance with an exemplary embodiment.

As described above, the X-ray source 110 emits broadband X-rays containing a plurality of energy bands to acquire a multi-energy image. The comparator 132 compares electrical signals of raw pixels constituting a virtual pixel with preset reference values. In this case, the preset reference values correspond to a plurality of energy bands respectively. An electrical signal generated by photons which are introduced into the X-ray detector 120 varies based on the energy of photons, i.e. the energy of X-rays. Thus, when voltage signals corresponding to the respective energy bands are preset to reference values based on an interrelationship between an electrical signal and the energy of X-rays, the comparator 132 may separate the raw pixels included in the single virtual pixel for a plurality of energy bands by comparing the electrical signals of the raw pixels with the preset reference values. The case in which the reconstructor 131 reconstructs the raw pixels of 6×6 into a single virtual pixel will be described below in detail by way of example.

FIG. 11 shows only a portion corresponding to a single virtual pixel. Referring to FIG. 11, the reconstructor 131 reconstructs raw pixels of 6×6 into a single virtual pixel, and the comparator 132 compares electrical signals of the raw pixels with preset reference values.

For example, in order to separate the raw pixels for three energy bands (first energy band, second energy band, and third energy band), the comparator 132 compares electrical signals of the raw pixels with a first reference value corresponding to the first energy band, a second reference value corresponding to the second energy band, and a third reference value corresponding to the third energy band, thereby separating the raw pixels for each energy band.

Each of the reference values may have an upper limit reference value or a lower limit reference value. When comparing the electrical signals of the raw pixels with an upper limit reference value or a lower limit reference value corresponding to each energy band, the comparator 132 may separate first energy pixels, second energy pixels, and third energy pixels from the raw pixels as exemplarily shown in the right side of FIG. 11.

Here, the first energy pixels mean raw pixels that may be estimated as receiving photons having energy of the first energy band, the second energy pixels mean raw pixels that may be estimated as receiving photons having energy of the second energy band, and the third energy pixels mean raw pixels that may be estimated as receiving photons having energy of the third energy band.

The counter 133 counts the number of raw pixels separated for each energy band. The comparator 132 and the counter 133 implement the above-described operation on all of the reconstructed virtual pixels.

Figure 12:
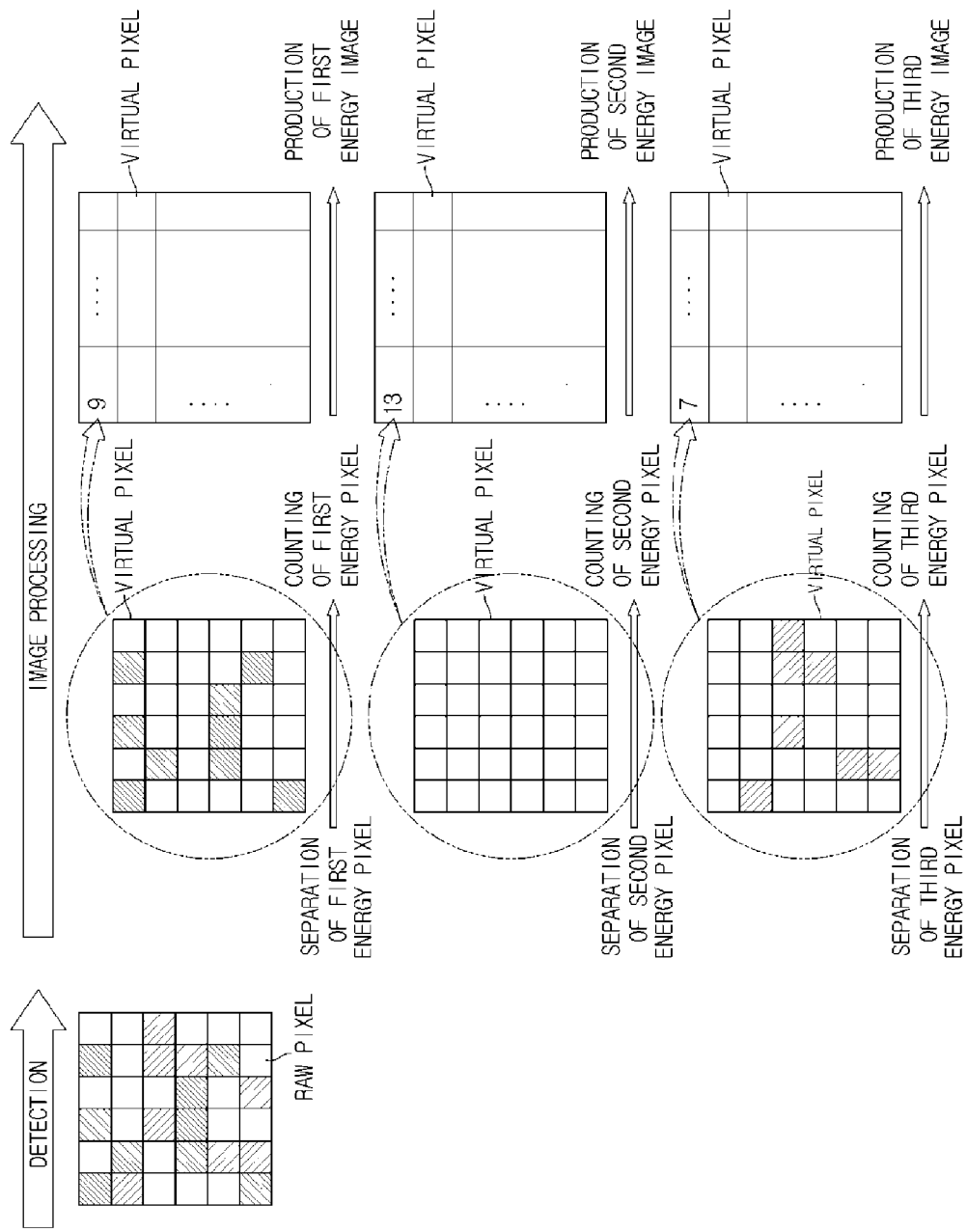
FIG. 12 is a view schematically showing the production of a single-energy image based on the number of pixels for each low energy band in accordance with an exemplary embodiment.

FIG. 12 is a view schematically showing the production of a single-energy image based on the number of pixels for each low energy band in accordance with an exemplary embodiment.

As described above, one photon or less is introduced into a single raw pixel. Thus, it can be said that an electrical signal of the raw pixel is generated by a single photon, and the number of raw pixels counted by the counter 133 may be estimated as the number of photons introduced into a single virtual pixel.

The single-energy image producer 134 produces a single-energy image constructed by virtual pixels per each of a plurality of energy bands by estimating the counted number of raw pixels as the number of photons introduced into the virtual pixel.

When image data transmitted from the X-ray detector 120 has a 2D pixel array of m×n, a single-energy image as exemplarily shown in FIG. 12 has a pixel array of m/6×n/6. As exemplarily shown in FIG. 12, when the counter 133 counts nine (9) first energy pixels included in any one virtual pixel, the single-energy image producer 134 may set a pixel value of the corresponding virtual pixel, i.e. a brightness value, to 9.

Since the comparator 132 and the counter 133 implement separation and counting of the raw pixels with respect to all virtual pixels, the single-energy image producer 134 may produce a first energy image by estimating the number of first energy pixels included in the other virtual pixels as the number of photons included in a first energy band.

When the counter 133 counts 13 second energy pixels included in any one virtual pixel, the single-energy image producer 134 may set a pixel value of the corresponding virtual pixel to 13. Then, the single-energy image producer 134 may produce a second energy image by estimating the number of second energy pixels included in the other virtual pixels as the number of photons included in a second energy band.

In addition, when the counter 133 counts seven (7) third energy pixels included in any one virtual pixel, the single-energy image producer 134 may set a pixel value of the corresponding virtual pixel to seven (7). Then, the single-energy image producer 134 may produce a third energy image by estimating the number of third energy pixels included in the other virtual pixels as the number of photons included in a third energy band.

Referring again to FIG. 9, when the X-ray detector 120 includes raw pixels of m×n and p raw pixels are reconstructed into a single virtual pixel, the single-energy image producer 134 may produce single-energy images each having a pixel array of m/p×n/p.

In the X-ray imaging apparatus 100, after X-rays are detected using the X-ray detector 120, which has a general charge integration type circuit configuration without including a photon counting circuit per pixel, the image processor 130 may separate X-rays or photons on a per energy band basis.

Figure 13:
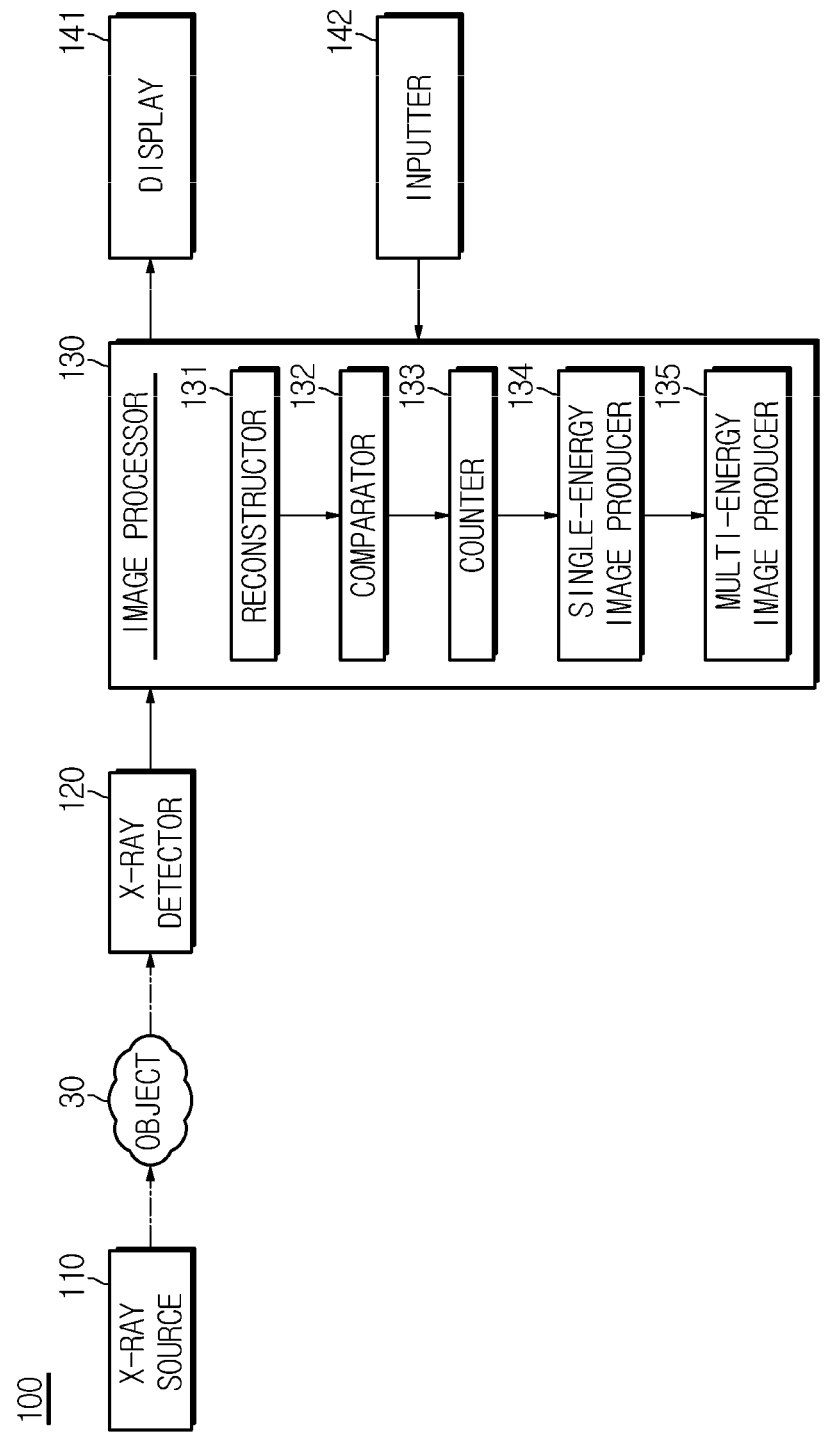
FIG. 13 is a control block diagram of the X-ray imaging apparatus further including a multi-energy image producer in accordance with an exemplary embodiment.

FIG. 13 is a control block diagram of the X-ray imaging apparatus further including a multi-energy image producer in accordance with an exemplary embodiment.

Referring to FIG. 13, the image processor 130 may further include a multi-energy image producer 135 to produce a multi-energy image having enhanced contrast between substances constituting an object by using a single-energy image for each energy band.

In one example, a multi-energy image produced by the multi-energy image producer 135 may be an image of a substance which makes up object. When an object is the chest and the single-energy image producer 134 produces a low energy image and a high energy image, the multi-energy image producer 135 may produce a bone image or a soft tissue image via dual energy X-ray subtraction.

Here, low energy and high energy are relative concepts, and may vary based on kinds or properties of the objects. For example, when an object is the chest, the maximum energy of a low energy band may be 70 keV and a maximum energy of a high energy band may be 140 keV. When an object is the breast, a maximum energy of a low energy band may be 30 keV and a maximum energy of a high energy band may be 70 keV.

Dual energy X-ray subtraction is a method of separating (or extracting) a selected one of bones and soft tissues by taking the log of an image acquired at a high energy level and an image acquired at a low energy level, and thereafter calculating a difference between the two images via the addition of appropriate weighting values. The weighting values added to the logarithmic images may be determined based on a difference between attenuation coefficients of bones and soft tissues depending on the energy value of the X-rays.

Alternatively, when an object is the breast and the comparator 132 separates raw pixels for three energy bands (low energy band, medium energy band, high energy band), the multi-energy image producer 135 may separate three substances which make up the breast.

One example of a substance separation method that may be adopted in the multi-energy image producer 135 will now be described in detail. The above Equation 1 describes a relationship between the intensity of X-rays and the attenuation coefficient of a substance. Assuming that X-rays having energy E penetrate M kinds of substances and a thickness of an $n^{th}$ substance (n being a natural number of M or less) is Tn, Equation 1 may be rewritten as the following Equation 2.

$$I = I_0 * e^{-\{\mu 1(E)T1 + \mu 2(E)T2 + \ldots + \mu M(E)TM\}} \qquad \text{Equation 2}$$

The intensity of the X-rays may be represented by the number of photons. A pixel value of an image is determined by dividing both sides of Equation 2 by a measurable $I_0$ and taking a −log value. In the same manner, when L X-ray images are acquired with respect to L different energy $E_1$, $E_2, \ldots, E_L$, a pixel value $P(E_1)$ may be represented by the following Equation 3.

$$P(E_1) = -\log(I(E_1)/I_0) \qquad \text{Equation 3}$$
$$= \mu_1(E_1)T_1 + \mu_2(E_1)T_2 + \ldots + \mu_M(E_1)T_M$$

Thus, L Equations such as the above Equation 3 with regard to each pixel may be acquired from L single-energy images. This may be represented in a matrix by the following Equation 4.

$$P = \mu \cdot T \qquad \text{Equation 4}$$

Thus, when L=M, an image separated for each substance may be acquired by calculating a matrix equation of $T = \mu^{-1} \cdot P$. Although the above Equation 4 is acquired under the assumption of an ideal monochromatic X-ray image, Equation 4 may be appropriately changed when using an X-ray image having a given energy band.

The above described method is only one example of methods that may be adopted in the multi-energy image producer 135. Various methods, for example, a method of acquiring differences between a low energy image, middle energy image, and high energy image via the addition of appropriate weighting values, and a method of separating a plurality of substances constituting an object using a plurality of single-energy images for each of the different energy bands, may be adopted.

The multi-energy image producer 135 may apply a post-treatment for various X-ray images to the multi-energy image, and display the resulting image via the display 141. The post-treatment of the present exemplary embodiment means a treatment applied after production of an X-ray image containing information regarding the number of photons introduced into each pixel, such as image reversal, noise removal, edge reinforcement, contrast adjustment, etc.

In a detailed example, gray-scale and frequency response of an image may be adjusted via gray-scale and frequency processing, and the quality of a diagnostic image may be improved via spatial frequency processing. In addition, objective image emphasis may be realized via gray-scale processing.

Meanwhile, the single-energy image producer 134 may apply post-treatment to a single-energy image per energy band, and display the resulting image via the display 141.

Although the above exemplary embodiment has described reconstructing a plurality of raw pixels into a single virtual pixel and separating the raw pixels included in the single virtual pixel per a plurality of energy bands, the exemplary embodiment of the X-ray imaging apparatus 100 is not limited thereto.

More specifically, without reconstruction of the raw pixels into the single virtual pixel, the raw pixels may be separated for a plurality of energy bands to produce a single-energy image per energy band and a multi-energy image.

Alternatively, a single-energy image may be produced by reconstructing a plurality of raw pixels into a single virtual pixel without separation of the raw pixels for each of a plurality of energy bands. To this end, the image processor 130 compares electrical signals of the raw pixels included in the virtual pixel with preset reference values to produce the single-energy image. More specifically, among the raw pixels included in the single virtual pixel, the number of raw pixels each having an electrical signal greater than a preset reference value may be estimated as the number of photons introduced into the single virtual pixel. The preset reference value may be a lower limit of an energy band corresponding to the single-energy image to be produced.

Hereinafter, a control method for the X-ray imaging apparatus in accordance with an exemplary embodiment will be described. The X-ray imaging apparatus 100 in accordance with the above described exemplary embodiment may be applied to the control method for the X-ray imaging apparatus in accordance with an exemplary embodiment.

Figure 14:
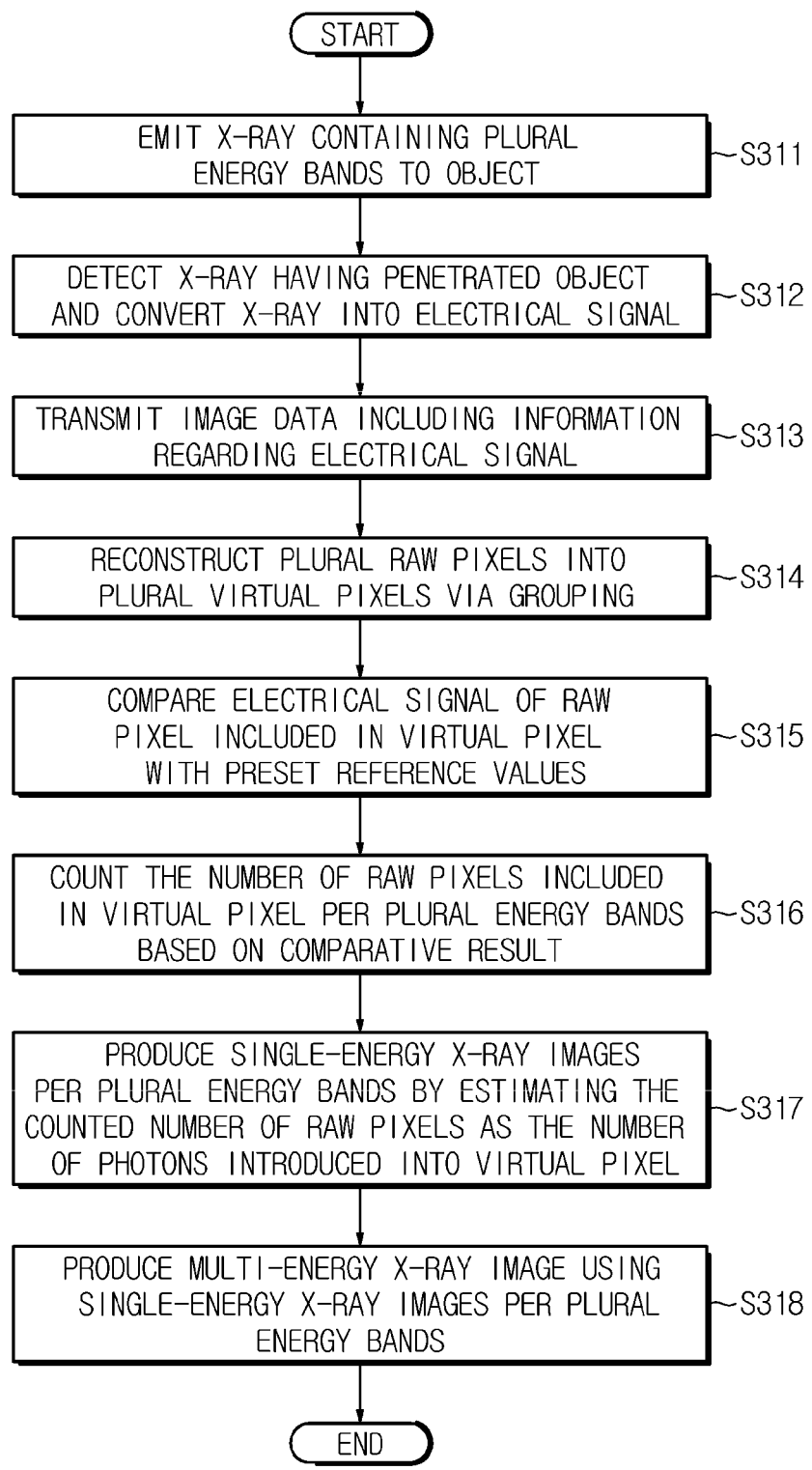
FIG. 14 is a flowchart of a control method for an X-ray imaging apparatus in accordance with an exemplary embodiment.

FIG. 14 is a flowchart of a control method for an X-ray imaging apparatus in accordance with an exemplary embodiment. In the present exemplary embodiment, a multi-energy X-ray image of an object is produced.

Referring to FIG. 14, first, X-rays containing a plurality of energy bands are emitted to an object (S311). That is, broadband X-rays are emitted. The plurality of energy bands may be different energy bands, in which at least one of an upper limit and a lower limit differ from one another. A range of each energy band may be preset based on properties or kinds of objects, image capture methods or purposes, etc.

X-rays which have penetrated the object are detected and converted into an electrical signal (S312). The detection of X-rays and conversion of the X-rays to the electrical signal are implemented by the X-ray detector 120 which includes a plurality of raw pixels. The raw pixels of the X-ray detector 120 have a small size so that a number of photons, e.g. on average 10 photons or less, are introduced. In a detailed example, the raw pixels may have a size for introduction of one photon or less on average. In addition, in order to introduce one photon or less into each raw pixel of the X-ray detector 120, a tube current, upon X-ray emission, may be adjusted to a preset value or less.

Image data including information regarding the electrical signal is transmitted to the image processor 130 (S313). The image data is a set of raw pixel data constituting the X-ray detector 120, and the raw pixel data contains information regarding the electrical signal. In addition, the raw pixel data may also contain position information of a corresponding raw pixel based on the format of image data.

The raw pixels are reconstructed into a plurality of virtual pixels via grouping (S314). As described above, since each raw pixel has a small size for introduction, for example, one photon or less on average, the image processor 130 may reconstruct the raw pixels into the virtual pixels by grouping the raw pixels by a preset number. The number of raw pixels to be reconstructed into a single virtual pixel may be set by the image processor 130, or may be set based on a user instruction.

Electrical signals of the raw pixels included in the virtual pixel are compared with preset reference values (S315). The preset reference values correspond to the a plurality of energy bands respectively. The raw pixels included in the single virtual pixel may be separated per the a plurality of energy bands by comparing the electrical signals of the raw pixels with the preset reference values.

Based on the comparative result, the number of raw pixels included in the virtual pixel is counted for each of the a plurality of energy bands (S316). That is, the number of raw pixels separated for each of the plurality of energy bands is counted, and separation and counting of the raw pixels are implemented on all of the virtual pixels.

Single-energy images for each of the a plurality of energy bands are produced by estimating the counted number of raw pixels as the number of photons introduced into the virtual pixel (S317). As described above, since one photon or less is introduced into a single raw pixel, an electrical signal of the raw pixel is generated by a single photon. Thus, single-energy images for each of the plurality of energy bands may be produced by estimating the counted number of raw pixels as the number of photons introduced into the virtual pixel, and setting a pixel value of the virtual pixel constituting each single-energy image to a value corresponding to the counted number of raw pixels.

A multi-energy image is produced using the single-energy images for each of the plurality of energy bands (S318). The multi-energy image is an image having enhanced contrast between substances constituting the object, and may be produced using differences between attenuation coefficients of the substances based on the energy of X-rays. For example, a multi-energy image may be an image of bones separated from the chest or a tissue image of soft tissues separated from the chest. Also the multi-energy image may be an image of fibroglandular tissues separated from the breast, an image of lesions separated from the breast, or an image of adipose tissues separated from the breast. In addition, the produced multi-energy image may be subjected to various post-treatments, and then displayed via the display 141.

In the control method of the X-ray imaging apparatus in accordance with an exemplary embodiment, single-energy images for each of a plurality of energy bands and a multi-energy image may be produced by separating a plurality of raw pixels for each energy band without reconstruction of the raw pixels into a single virtual pixel.

Figure 15:
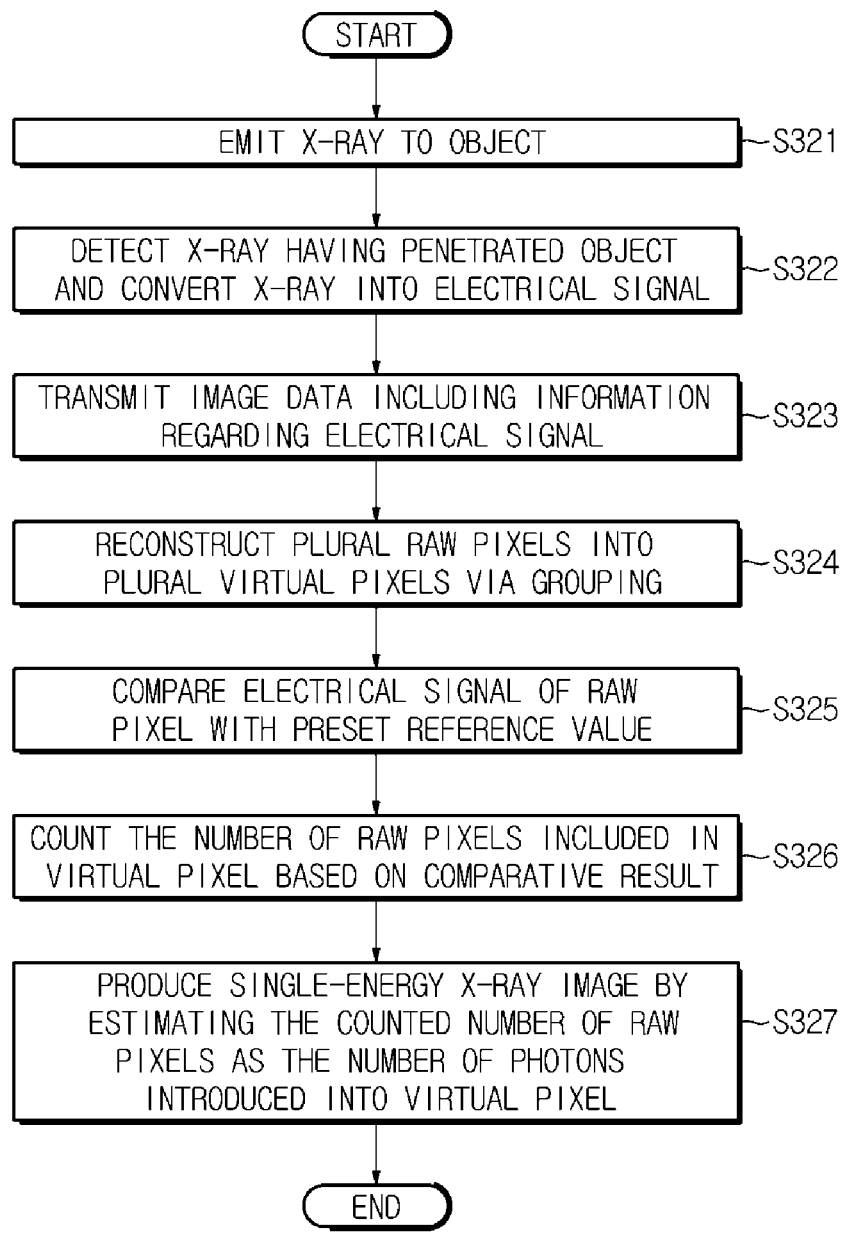
FIG. 15 is a flowchart of a control method for an X-ray imaging apparatus to produce a single-energy image in accordance with an exemplary embodiment.

FIG. 15 is a flowchart of a control method for an X-ray imaging apparatus in accordance with another exemplary embodiment.

A control method of an X-ray imaging apparatus in accordance with the present exemplary embodiment may be used to produce a single-energy image.

First, X-rays are emitted to an object (S321). In this case, the emitted X-rays are not broadband X-rays containing a plurality of energy bands as described above, but are X-rays having a single energy band, i.e. an energy band to produce a single-energy image. The energy band of the emitted X-rays may be preset based on properties or kinds of objects, image capture methods or purposes, etc.

The X-rays which have penetrated the object are detected and converted into an electrical signal (S322), and image data including information regarding the electrical signal is transmitted to the image processor (S323). A description related thereto is similar to the above description with reference to FIG. 14.

A plurality of raw pixels are reconstructed into a plurality of virtual pixels via grouping (S324), and an electrical signal for each raw pixel is compared with a preset reference value (S325). In this case, the preset reference value corresponds to a selected energy band. To produce an X-ray image using photons included in an energy band of E1 or more, a reference value corresponding to E1 is preset and compared with the electrical signal of each raw pixel. E1 may be a lower limit of the energy band of the emitted X-rays, or may be a different value from the lower limit.

Based on the comparative result, the number of raw pixels included in a single virtual pixel is counted (S326). A single-energy image is produced by estimating the counted number of raw pixels as the number of photons introduced into the virtual pixel (S327). As described above, since one photon or less is introduced into each raw pixel, the number of raw pixels included in the virtual pixel may be estimated as the number of photons introduced into the corresponding virtual pixel. Thus, the single-energy image may be produced by setting a pixel value of the virtual pixel constituting the single-energy image to a value corresponding to the counted number of raw pixels. Then, the produced single-energy image may undergo various forms of post-treatment and are then displayed on the display 141.

As is apparent from the above description, in an X-ray imaging apparatus and a control method for the same in accordance with the above described exemplary embodiments, through use of an X-ray detector having a charge integration type circuit configuration, it may be possible to realize a large-area X-ray detector and to eliminate a counting circuit per pixel of the X-ray detector, which may result in a considerably enhanced production yield of the X-ray detector and reduced manufacturing costs.

In addition, it may be possible to acquire a multi-energy image of an object via a single X-ray exposure, which may minimize the amount of radiation exposure of the object and minimize the amount of power loading for an X-ray source.

Further, X-rays may be detected using a circuit structure which is applied to typical electron accumulation without requiring a counting circuit per pixel. Photons are counted to produce an X-ray image for each energy band, which may result in the production of a multi-energy image having an enhanced contrast between substances.

Although the exemplary embodiments have been shown and described, it would be appreciated by those skilled in the art that changes may be made in these exemplary embodiments without departing from the principles and spirit of an exemplary embodiment, the scope of which is defined in the claims and their equivalents.

What is claimed is:

1. An X-ray imaging apparatus comprising:
   an X-ray source configured to generate and emit X-rays having a preset broadband;
   an X-ray detector including a plurality of raw pixels, each of the plurality of raw pixels being configured to detect photons in response to the emitted X-rays, and convert the detected photons into electrical signals; and
   an image processor configured to generate a plurality of single-energy images corresponding to respective energy bands, by separating the plurality of raw pixels for the respective energy bands based on the electrical signals, and generate a multi-energy image using the plurality of single-energy images,
   wherein the X-ray detector is configured to detect the photons according to a charge integration mode in which charges introduced into the raw pixels for a given time are accumulated and thereafter, the electrical signals are acquired from the accumulated charges,
   wherein the image processor is configured to generate the plurality of single-energy images by grouping the plurality of raw pixels into a plurality of virtual pixels, and estimating a number of the photons for each of the plurality of virtual pixels as a number of the plurality of raw pixels separated for each of the plurality of virtual pixels.

2. The apparatus according to claim 1, wherein the image processor is configured to reconstruct the plurality of raw pixels into the plurality of virtual pixels by grouping the plurality of raw pixels according to a preset number.

3. The apparatus according to claim 2, wherein the image processor is configured to compare the electrical signals of the plurality of raw pixels included in each of the plurality of virtual pixels with reference values corresponding to the respective energy bands in order to separate the plurality of raw pixels for the respective energy bands.

4. The apparatus according to claim 1, wherein the image processor is configured to count the number of the plurality of raw pixels separated for each of the energy bands in each of the plurality of virtual pixels.

5. The apparatus according to claim 1, wherein the image processor is configured to count the number of the plurality of raw pixels separated for the respective energy bands, and generate each of the plurality of single-energy images by setting brightness values for the plurality of virtual pixels to be equal to the number of the plurality of raw pixels counted in the plurality of virtual pixels, respectively.

6. The apparatus according to claim 2, further comprising an inputter configured to receive an instruction with regard to the number of the plurality of raw pixels to be reconstructed into each of the plurality of virtual pixels,
   wherein an input number of the plurality of raw pixels is preset as the number of the plurality of raw pixels constituting one virtual pixel.

7. The apparatus according to claim 1, wherein the plurality of raw pixels of the X-ray detector are active pixels and wherein each of the plurality of raw pixels includes an active circuit to amplify the electrical signals, respectively.

8. The apparatus according to claim 1, wherein an X-ray exposure time or a tube current of the X-ray source is adjusted to allow an average of ten photons or less to be introduced for each raw pixel of the plurality of raw pixels of the X-ray detector.

9. The apparatus according to claim 1, wherein the X-ray detector includes an oxide Thin Film Transistor (TFT).

10. The apparatus according to claim 1, wherein the X-ray detector is a Complementary Metal Oxide Semiconductor (CMOS) detector.

11. The apparatus according to claim 1, wherein the X-ray detector is an indirect detector comprising:
    a scintillator configured to convert the emitted X-rays into visible light; and a photodiode configured to convert the visible light into the electrical signals.

12. The apparatus according to claim 1, wherein the X-ray detector is a direct detector comprising a photoconductor configured to convert the emitted X-rays into the electrical signals.

13. The apparatus according to claim 1, wherein the X-rays having the preset broadband are X-rays containing the respective energy bands.

14. The apparatus according to claim 1, wherein the multi-energy image is an image of at least one substance of a plurality of substances constituting an object toward which the X-rays are emitted.

15. An X-ray imaging apparatus comprising:
an X-ray source configured to generate and emit X-rays having a preset energy band;
an X-ray detector including a plurality of raw pixels configured to detect photons in response to the emitted X-rays and convert the detected photons into electrical signals; and
an image processor configured to generate a single-energy image by reconstructing the plurality of raw pixels into a plurality of virtual pixels by grouping the plurality of raw pixels, counting the plurality of raw pixels in the plurality of virtual pixels, respectively, by comparing respective electrical signals of the plurality of raw pixels included in each of the plurality of virtual pixels with a reference value, and estimating a number of the photons for each of the plurality of virtual pixels as a number of the plurality of raw pixels counted in each of the plurality of virtual pixels,
wherein the X-ray detector is configured to detect the photons according to a charge integration mode in which charges introduced into the raw pixels for a given time are accumulated and thereafter, the electrical signals are acquired from the accumulated charges.

16. The apparatus according to claim 15, wherein the image processor is configured to estimate the number of photons introduced into the plurality of virtual pixels, as the number of the plurality of raw pixels having a greater electrical signal than the reference value, among the plurality of raw pixels included in each of the plurality of virtual pixels, respectively.

17. A control method for an X-ray imaging apparatus, the control method comprising:
emitting X-rays having a preset broadband;
detecting, with an X-ray detector, photons included in the emitted X-rays, for each of a plurality of raw pixels of the X-ray detector, and converting the detected photons into electrical signals;
separating the plurality of raw pixels for respective energy bands based on the electrical signals;
generating a plurality of single-energy images corresponding to the respective energy bands, by grouping the plurality of raw pixels into a plurality of virtual pixels, and estimating a number of the photons for each of the plurality of virtual pixels as a number of the plurality of raw pixels separated for each of the plurality of virtual pixels; and
generating a multi-energy image using the plurality of single-energy images.

18. The control method according to claim 17, further comprising:
reconstructing the plurality of raw pixels into the plurality of virtual pixels by grouping the plurality of raw pixels according to a preset number.

19. A control method for an X-ray imaging apparatus, the control method comprising:
generating and emitting X-rays having a preset energy band;
detecting, by an X-ray detector, photons included in the X-rays, for each of a plurality of raw pixels of the X-ray detector, and converting the detected photons into electrical signals;
reconstructing the plurality of raw pixels into a plurality of virtual pixels by grouping the plurality of raw pixels according to a preset number;
counting a number of the plurality of raw pixels included in the plurality of virtual pixels, respectively, by comparing the electrical signals of the plurality of raw pixels included in each of the plurality of virtual pixels with a reference value; and
generating a single-energy image by estimating a number of the photons in each of the plurality of virtual pixels as the number of the plurality of raw pixels counted in the plurality of virtual pixels, respectively.

20. The control method according to claim 19, wherein the number of photons comprises:
estimating the number of photons as the number of raw pixels having a greater electrical signal than the reference value, among the plurality of raw pixels included in each of the plurality of virtual pixels, respectively.

21. An X-ray imaging apparatus comprising:
an X-ray source configured to generate and emit X-rays having a preset energy band,
an X-ray detector including a plurality of raw pixels, each of the plurality of raw pixels being configured to detect photons in response to the emitted X-rays and convert the detected photons into electrical signals; and
an image processor configured to generate a single-energy image by reconstructing the plurality of raw pixels into a plurality of virtual pixels by grouping the plurality of raw pixels according to a preset number, counting a number of the plurality of raw pixels included in the plurality of virtual pixels by comparing the electrical signals of the plurality of raw pixels included in each of the plurality of virtual pixels with a reference value, and estimating a number of the photons for each of the plurality of virtual pixels as a number of the plurality of raw pixels counted in each of the plurality of virtual pixels.

22. A control method for an X-ray imaging apparatus, the method comprising:
generating and emitting X-rays having a preset energy band;
detecting, with an X-ray detector, photons included in the emitted X-rays, for each pixel of a plurality of raw pixels of the X-ray detector, and converting the detected photons into electrical signals;
reconstructing the plurality of raw pixels into a plurality of virtual pixels by grouping the plurality of raw pixels according to a preset number;
counting a number of the plurality of raw pixels included in the plurality of virtual pixels, respectively, by comparing the electrical signals of the plurality of raw pixels included in each of the plurality of virtual pixels with a reference value; and
generating a single-energy image by estimating a number of the photons in each of the plurality of virtual pixels as the number of the plurality of raw pixels counted in the plurality of virtual pixels, respectively.

* * * * *